(12) United States Patent
Babish et al.

(10) Patent No.: US 6,780,596 B2
(45) Date of Patent: Aug. 24, 2004

(54) METHODS FOR DETERMINING THE ACTIVITY OF COMPLEX MIXTURES

(75) Inventors: John G. Babish, Brooktondale, NY (US); Linda M. Pacioretty, Brooktondale, NY (US); M. Lisa Lee, Dryden, NY (US)

(73) Assignee: Ashni Naturaceuticals, Inc., Salt Lake City, UT (US)

(*) Notice: Subject to any disclaimer, the term of this patent is extended or adjusted under 35 U.S.C. 154(b) by 0 days.

(21) Appl. No.: 09/156,741

(22) Filed: Sep. 17, 1998

(65) Prior Publication Data

US 2001/0039022 A1 Nov. 8, 2001

(51) Int. Cl.[7] .................. G01N 33/03; G01N 33/567; G01N 33/574; C12Q 1/42; C12Q 1/40
(52) U.S. Cl. .................. 435/7.1; 435/7.1; 435/7.2; 435/7.21; 435/7.23; 435/21; 435/28; 435/69.3; 435/70.3; 435/410; 436/512; 436/513; 436/516; 436/517; 436/518
(58) Field of Search .................. 435/7.1, 7.2, 7.21, 435/7.23, 21, 28, 69.3, 69.4, 70.3; 436/512, 513, 516, 517, 18

(56) References Cited

U.S. PATENT DOCUMENTS

| | | | |
|---|---|---|---|
| 4,543,439 A | * | 9/1985 | Frackelton, Jr. et al. ...... 935/92 |
| 4,696,315 A | | 9/1987 | Summers |
| 4,871,661 A | | 10/1989 | Webb et al. .................. 435/7 |
| 5,260,200 A | * | 11/1993 | Kahn et al. .................. 435/68.1 |
| 5,378,465 A | * | 1/1995 | Zeines ..................... 424/195.1 |
| 5,447,852 A | | 9/1995 | Friedman et al. |
| 5,496,703 A | * | 3/1996 | Babish et al. .............. 435/7.21 |
| 5,532,167 A | | 7/1996 | Cantley et al. ............... 436/89 |
| 5,585,233 A | | 12/1996 | Moller et al. |
| 5,599,681 A | * | 2/1997 | Epstein et al. ............. 435/7.23 |
| 5,618,677 A | | 4/1997 | Ni et al. .................... 435/7.1 |
| 5,621,075 A | * | 4/1997 | Kahn et al. .................. 530/350 |
| 5,624,808 A | | 4/1997 | Thompson et al. ......... 435/7.24 |
| 5,672,470 A | | 9/1997 | Hengstenberg et al. ....... 435/4 |
| 5,695,944 A | | 12/1997 | Croce et al. ............... 435/7.21 |
| 5,763,198 A | * | 6/1998 | Hirth et al. ................ 435/7.21 |

OTHER PUBLICATIONS

US 5,694,944, 12/1997, Croce et al. (withdrawn)*
Epstein et al. 1990. J. of Bio. Chem. 265(18): 10746–751.*
Towbin et al. 1979. PNAS. 76(9): 4350–54.*

(List continued on next page.)

*Primary Examiner*—Mark Navarro
*Assistant Examiner*—J. Hines
(74) *Attorney, Agent, or Firm*—Kenyon & Kenyon

(57) ABSTRACT

According to the present invention, the biological or pharmacological activity of a test material like a plant or herbal material, an extract of a plant or herbal material, a natural or synthetic compound or some combination thereof, can be quantified by observing the pattern of structural changes induced in a eukaryotic cell's proteins. These structural changes may be evidenced by protein phosphorylation, by protein-protein interactions and the like. The amount and nature of protein phosphorylation is qualitatively and quantitatively related to the in vitro concentration of biologically/pharmacologically active components to which the mammalian cells are exposed. Additionally, formation or loss of protein-protein complexes may be determined in whole cell homogenates through the use of non-denaturing electrophoresis and staining for proteins or protein phosphorylation. The present invention allows natural products to be formulated into nutritional supplements and pharmacological preparations of consistent biological/pharmacological activity without the need to identify any of the chemical constituents responsible for the biological or pharmacological response.

13 Claims, 11 Drawing Sheets

OTHER PUBLICATIONS

Ammann et al., *Fluoride Potentiates the Osteogenic Effects of IGF–I in Aged Ovarectomized Rats*, 22 Bone 39 (1998).

Dong et al., *Activation of tumoricidal properties in macrophages by lipopolysaccharide requires protein–tyrosine kinase activity*, 53 J. Leukocyte Biol. 53 (1993).

German Torres & Judith Horowitz, *Individual and Combined Effects of Ethanol and Cocaine on Intracellular Signals and Gene Expression*, in 20 Prog. Neuro–Psychopharmacol. & Biol. Psychiat. 561 (1996).

Markovac et al., *Lead Activates Protein Kinase C in Immature Rat Brain Microvessels*, 96 Toxicol. & App. Pharm. 14 (1988).

Newstad et al., *Effect of 2, 3, 7, 8–Tetrachlorodibenzo–p–dioxin (TCDD) on the Epidermal Growth Factor Receptor in Hepatic Plasma Membranes of Rainbow Trout (Oncorhynchus mykiss)*, 119 Toxicol. & App. Pharm. 41 (1993).

Schieven et al., *Lineage–specific Induction of B Cell Apoptosis and Altered Signal Transduction by Phosphotyrosine Phosphatase Inhibitor Bis(Maltolato)oxovanadium (IV)* 270 J. Biol. Chem. 20824 (1995).

Traxler et al., *Use of a Pharmacophore Model for the Design of EGF–R Tyrosine Kinase Inhibitors: 4–(Phenylamino)Pyrazolo [3,4–d] pyrinidines*, 40 J. Med. Chem. 3601 (1997).

Wipf et al., *Combinatorial Synthesis and Biological Evaluation of Library of Small–Molecule Ser/Thr–Protwin Phosphatase Inhibitors*, Bioorganic & Medicinal Chemistry 165 (1997).

\* cited by examiner

METHODS FOR DETERMINING THE ACTIVITY OF COMPLEX MIXTURES

FIELD OF THE INVENTION

The present invention is directed to a method for assessing the biological or pharmacological activity of a test material without the need to identify any of the constituents of that material, by exposing mammalian cells to the material and assessing whether structural changes, such as protein phosphorylation or protein-protein interaction, are induced in proteins present in the mammalian cells. While the present methods are useful for any test material, these methods have particular utility for testing materials which include complex mixtures of molecules where, for example, the physiological effects of the complex mixture may be a result of a synergy between two or more constituents present in the mixture. Thus, the present methods can be used to assess the biological activity of herbs, herbal extracts, plant extracts, animal extracts, natural or synthetic compounds, or combinations thereof. This method facilitates the formulation of natural products with consistent biological or pharmacological activities without the need to identify any of the chemical constituents responsible for the biological or pharmacological response.

BACKGROUND OF THE INVENTION

Modern medical and pharmaceutical sciences typically attempt to treat disease by prescription of a single, highly purified and well-characterized pharmaceutical compound whose activity has been carefully measured so that a precise dosage may be administered. The use of such highly purified drugs facilitates the manufacture of uniform dosage forms because drug concentration can simply and accurately be used to predict the appropriate pharmacological dosage.

However, use of a single highly purified drug is not always appropriate nor desirable for treating disease. In some instances, nutrients and/or pharmacologically active compounds may act together, in synergy. For example, research indicates that several constituents in saw palmetto extracts operate in synchrony to inhibit proliferation of cells in benign prostatic hyperplasia (BHP).

The most frequent reason men consult a urologist is because of an impairment in urinary flow. In men over 45 years of age, the cause of impaired urinary flow is often benign prostatic hyperplasia (BHP). The cause of BHP is an abnormal, but nonmalignant, proliferation of cells and tissues within the prostate gland. Eventually, urethral obstruction leads to urinary retention, kidney damage, and infection. In advanced stages, surgical resection is the treatment of choice.

To understand how medications may affect BPH, medical researchers seek the mechanism(s) that are believed to cause the condition. In the prostate, testosterone from the blood is converted by an enzyme to the more potent androgen, dihydrotestosterone (DHT). DHT increases the expression of proteins with resultant changes in cell metabolism and proliferation. In the process of normal growth, sex accessory organs are relatively insensitive to testosterone and DHT after puberty. However, in hyperplastic prostatic tissues the concentrations of DHT may be four to six times those of normal prostatic tissue. Thus, researchers infer that these high concentrations of DHT result in increased growth of the gland in mature males. Drugs have been developed to reduce the effects of androgens, for example, estrogens. However, while estrogens do reduce the effect of androgens they cause feminization, impotence, and cardiovascular toxicity in men—side effects which are highly undesirable.

In addition to androgenic stimulation, infiltration of the prostate by inflammatory cells is an etiologic factor in the development of BPH. These inflammatory cell types, such as polymorphonuclear neutrophils, produce chemotactic mediators and contribute to the development of the disease. Among the chemotactic factors generated by inflammatory cell types, derivatives of arachidonic acid have been extensively studied. Thus, medical research indicates that the best therapeutic regimen for BHP would address both androgenic and inflammatory mechanisms.

Several plants contain compounds with antiandrogenic and anti-inflammatory properties, for example, saw palmetto which consists of the partially dried, ripe fruit of *Serenoa repens*. Saw palmetto was recognized as a "drug" in the United States from 1906 to 1950 and was once widely used for a variety of ailments, particularly those of the urogenital tract, until losing popularity in the United States after World War II. European scientists continued to study saw palmetto and recognized that, in patients suffering form BPH, an extract of the fruit produced increased urinary flow, reduced residual urine, increased ease in commencing micturition, and decreased frequency of urination.

While extensive clinical and laboratory studies have been undertaken and reported, the mechanism of action of saw palmetto is poorly understood. Studies have shown that a liposterolic extract of the berries reduced cellular uptake of both testosterone and DHT by more than 40 percent. This mechanism is confirmed by the observation that saw palmetto extract does not induce changes in the level of testosterone, or other hormones, in the plasma. Other studies have indicated that an extract of saw palmetto reduces the conversion of less active testosterone to the more active DHT by inhibiting the enzyme 5α-reductase.

In addition to their antiandrogenic properties, saw palmetto berries may also have anti-inflammatory activity. This may to be due to the inhibition of the cyclooxygenase and 5-lipoxygenase pathways, thereby preventing the biosynthesis of inflammation-producing prostaglandins and leukotrienes. Together, the antiandrogenic and anti-inflammatory effects seem to account for the beneficial role of the herb in treating BPH. Placebo-controlled, double-blind clinical studies carried out on more than 2,000 BPH patients in Germany have confirmed the effectiveness of a saw palmetto extract in such conditions.

A large number of possibly active ingredients have been isolated from saw palmetto including large amounts of beta-sitosterol-3-D-glucoside. Anthranilic acid, caffeic acid, chorogenic acid, tannin, sugars, and polysaccharides, are also present. Unfortunately, the active antiandrogenic principles remain unidentified, although they are known to reside in the acidic lipophilic fraction of the berries. The inability to identify a single, active compound indicates that a combination of ingredients may be responsible for the beneficial activities of saw palmetto. Alteration of the combination through purification of single ingredients results in a concomitant loss of the original biological activity.

However, the pharmaceutical industry generally relies upon purifying and quantifying an active ingredient in order to standardize preparation of medications.

The present invention provides a solution to this problem by providing methods for assessing the biological activity of a test material without the need for identifying and quantifying the active constituents of the test material. According to the present invention, cellular health and function can be assessed by observing the type and amount of certain proteins in the cell. Thus, the methods of the present invention expose mammalian cells to a test material and assess whether new proteins are synthesized by the cell or structural changes are induced in cellular proteins.

Cellular function is a direct result of both transcriptional and translational control processes. It has long been recognized that transcriptional control is necessary to differentiate one cell type from another. However, in addition to the variety of transcriptional controls developed by cells, cellular function is also dependent on the type and amount of post-translational modification of cellular proteins. One such post-translational modification is protein phosphorylation. Phosphorylation of serine, threonine and tyrosine residues on proteins is a fundamental post-translational regulatory process for mediating signal transduction, gene transcription, RNA splicing, cellular adhesion, apoptosis and cell cycle control. Wipf et al., 5 BIOORGANIC & MEDICINAL CHEMISTRY 165 (1997). According to the present invention, the type and extent of structural changes in cellular proteins is a measure of the physiological state of a cell. Thus, the cell reacts to environmental stimuli by increasing or decreasing protein phosphorylation, and by reorganizing how proteins interact with each other.

Specific, individual compounds are known to increase protein phosphorylation. For example, fluoride has been shown to enhance protein tyrosine phosphorylation of various constituents in the intracellular signaling cascade of osteoblasts. Ammann et al., 22 BONE 39 (1998). Ethanol and cocaine have been shown to increase the phosphorylation rate of certain phosphoproteins. Torres & Horowitz, 20 PROG. NEURO-PSYCHOPHARMACOL. & BIOL. PSYCHIAT. 561 (1996). Lead may induce phosphorylation in brain cells. Markovac et al., 96 TOXICOL. & APP. PHARM. 14 (1988). Dioxin may induce protein phosphorylation in trout. Newstad et al., 119 TOXICOL. & APP. PHARM. 41 (1993).

Some methods for detecting or identifying certain types of molecules have been developed which utilize phosphorylated proteins. For example, U.S. Pat. No. 5,496,703 to Babish et al., issued Mar. 5, 1996, discloses methods for detecting dioxins by exposing mammalian cells to a test sample which may contain such dioxins, examining a cell lysate of the mammalian cells for the presence of phosphorylated proteins and correlating the phosphorylation level of those phosphorylated cells with a standard set of phosphorylated proteins derived from mammalian cells known to be exposed to dioxin or dioxin-like molecules. U.S. Pat. No. 5,695,944 to Croce et al., issued Dec. 9, 1997, is directed to a method of identifying compounds that modulate bcl-2 mediated cell death by contacting a cell with a test compound and detecting whether the bcl-2 in the cell is phosphorylated at a higher or lower level than a control cell which is not contacted with the test compound. U.S. Pat. No. 5,672,470 to Hengstenberg et al., issued Sep. 30, 1997, is drawn to a method for detecting toxic substances, by incubating a sample with a suspension of bacteria which have a phosphotransferase system so that a substrate analog is phosphorylated and then hydrolyzed by an enzyme in the phosphotransferase system. U.S. Pat. No. 5,618,677 to Ni et al., issued Apr. 8, 1997, is directed to a method of testing whether a compound modulates a phosphate cotransporter protein by exposing a cell with the human inorganic phosphate cotransporter protein to a test compound and measuring a change in inorganic phosphate uptake relative to a control cell which is not exposed to the test compound. U.S. Pat. No. 4,871,661 to Webb et al., issued Oct. 3, 1989, is directed to a method of screening materials for carcinogenic properties by administering those materials to test animals and observing whether the animal produces a 60 kilodalton cancer-associated phosphoprotein.

While the prior art discloses that protein tyrosine kinases, which phosphorylate proteins, play a fundamental role in signal transduction pathways and provides procedures for detecting phosphorylated proteins, these references do not disclose that complex mixtures of molecules are capable of producing reproducible signaling patterns of phosphoproteins, or that mammalian phosphorylation patterns may accordingly be used to assess the total biological activity of a complex mixture of molecules.

SUMMARY OF THE INVENTION

The present invention is directed to a method for determining whether a test material has biological activity which includes, incubating the test material with cultured mammalian cells to produce tested mammalian cells, lysing the tested mammalian cells, and comparing the pattern of phosphorylated proteins in those tested mammalian cells to the pattern of phosphorylated proteins in control cells. The test material can be a mixture of molecules, an herb, a mixture of herbs, an herbal extract, a plant extract and the like. The control cells are either the same cultured mammalian cells which have not been exposed to the test material or the same cultured mammalian cells which are in a quiescent, or non-dividing condition. In a further embodiment, the pattern of phosphorylated proteins in the tested mammalian cells may be compared to the pattern of phosphorylated proteins in positive control cells. Such positive control cells are the cultured mammalian cells which have been exposed to a known beneficial and non-toxic compound, an FDA approved drug or a beneficial plant or herbal extract of proven efficacy.

The present invention is also directed to a method for determining whether a test material has biological activity which includes, incubating the test material with cultured mammalian cells to produce tested mammalian cells, lysing the tested mammalian cells to produce a mixture of cellular proteins, electrophoretically-separating the cellular proteins, reacting the cellular proteins with a monoclonal antibody directed against a phosphorylated amino acid and comparing the pattern of phosphorylated proteins in the tested mammalian cells to the pattern of phosphorylated proteins in control cells. Again, the control cells are the same cultured mammalian cells which have not been exposed to the test material. The pattern of phosphorylated proteins in the these tested mammalian cells may also be compared to the pattern of phosphorylated proteins in positive control cells which have been exposed to a beneficial and non-toxic compound, an FDA approved drug or a beneficial plant or herbal extract of proven efficacy.

The present invention is further directed to a method for detecting synergy of biological activity between a first component and a second component in a complex mixture of components which comprises separating the complex mixture of components into a first fraction and a second fraction, and testing whether the first fraction induces the same pattern of protein phosphorylation as the complex mixture. In this instance, the first component is present in the first fraction and the second component is present in the second fraction.

The present invention is still further directed to a method for determining whether a first component has more biological activity than a second component of a complex mixture of components which includes separating the complex mixture of components into a first fraction and a second fraction, and testing whether the first fraction induces the same pattern of protein phosphorylation as the second fraction. Again, the first component is present in the first fraction and the second component is present in the second fraction.

The present invention is also directed to a method for determining whether a test material has biological activity which includes, incubating the test material with cultured mammalian cells to produce tested mammalian cells, lysing the tested mammalian cells, and comparing the pattern of protein-protein interaction in the tested mammalian cells to the pattern of protein-protein interaction in control cells. The control cells are the same cultured mammalian cells which have not been exposed to the test material. The protein-protein interaction in the tested mammalian cells may also be compared to the pattern of protein-protein interaction in positive control cells. Such positive control cells can be cultured mammalian cells which have been exposed to a beneficial and non-toxic compound such as an FDA approved drug, a beneficial plant or herbal extract of proven efficacy or the like.

The present invention is further directed to a method for comparing the biological activity of a test material to a control material which includes, incubating the test material with cultured mammalian cells to produce tested mammalian cells, lysing the tested mammalian cells, and comparing the pattern of phosphorylated proteins in the tested mammalian cells to the pattern of phosphorylated proteins in control cells. In this embodiment the control cells are the same cultured mammalian cells which have been exposed to a control material and have not been exposed to the test material. The control material is a beneficial and non-toxic compound such as an FDA approved drug, a beneficial plant or herbal extract of proven efficacy, or the like.

DETAILED DESCRIPTION OF THE INVENTION

Figure 1:
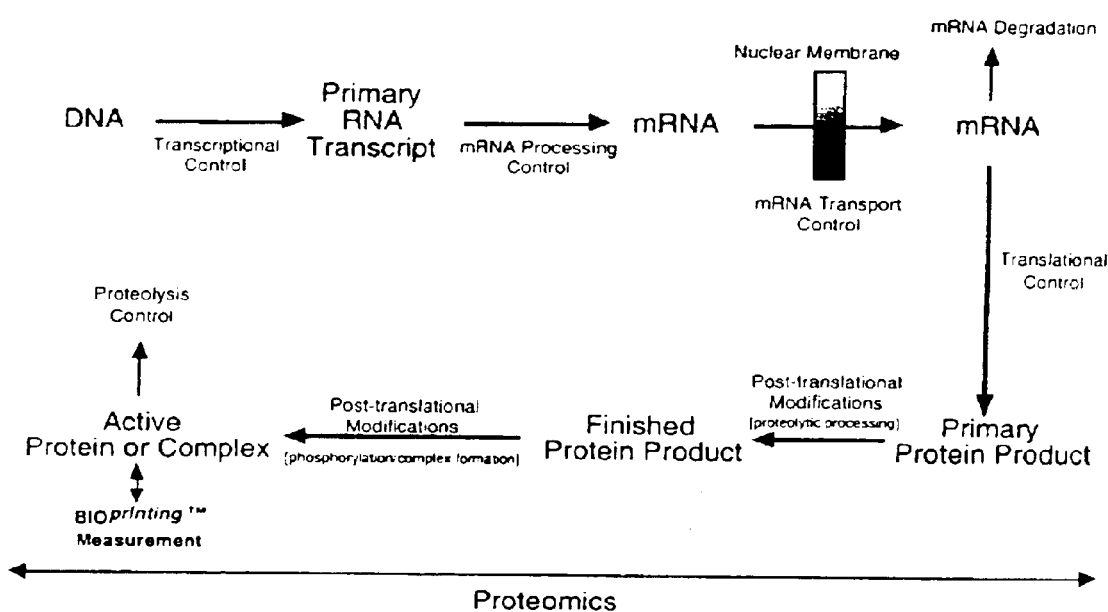
FIG. 1 provides a schematic diagram illustrating the process by which functionally active proteins are made in eukaryotic cells. DNA directs the synthesis of RNA, and RNA then directs the synthesis of protein. Special proteins catalyze and regulate the synthesis and degradation of both RNA and DNA. The DNA to RNA to protein, and then back to DNA cycle, has been called the "central dogma" of molecular biology. However, whereas DNA stores the information for protein synthesis and RNA carries out the instructions encoded in DNA, most biological activities are carried out by proteins. The synthesis of proteins and the ultimate structure of proteins are therefore at the heart of cellular function. As recognized by the present invention, protein structure reflects the status of the cell's health and its activity level.
Figure 2:
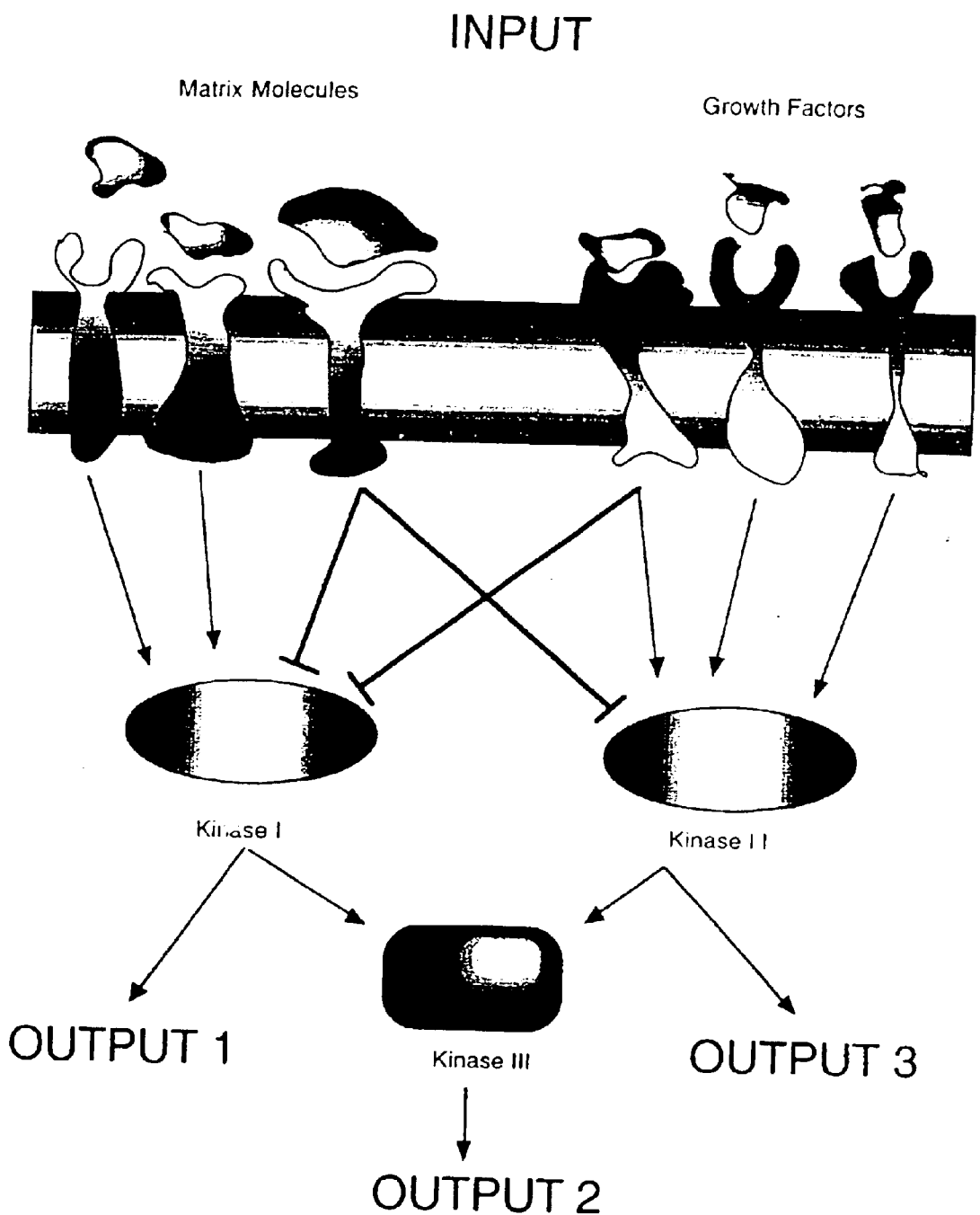
FIG. 2 depicts a simple hypothetical signaling network consisting only of six receptors and three cytosolic protein kinases for illustrative purposes. Each receptor activates or inhibits kinase 1 or 2 or both by an unspecified mechanism. Because signals converge into kinase 3, this network will be maximally active only when specific combinations of stimuli are present. Although this network is far simpler than any likely to be found in a living cell, it demonstrates the complex signaling network that functions to maintain homeostasis and coordinate the interaction of the cell with external matrix molecules. Our present knowledge is insufficient to accurately predict the pattern of response generated by any combination of matrix molecules.

According to the present invention, the type and amount of structural changes that cellular proteins undergo when exposed in vivo to a compound, or an extract or mixture of compounds, is related to whether that compound, extract or mixture has any biological or pharmacological activity. Moreover, according to the present invention, the type and amount of structural changes observed in eukaryotic cellular proteins are reproducible. This means that the amount of biological or pharmacological activity of a compound, or an extract or mixture of compounds, can be determined by quantifying how many structural changes are induced in the cellular proteins of cultured cells. Similarly, the activity of one preparation of the compound, or an extract or mixture containing several compounds, can be measured against that of another preparation, for example, a control preparation.

One of the benefits of the present invention is that this assessment of biological or pharmacological activity can be performed on a mixture of compounds or a complex extract of natural products, without the need to identify which component or components provide the activity. The present invention is therefore particularly useful for assessing the activity of complex mixtures where two or more unidentified components, which separately may have little or no activity, operate together to provide an unexpected synergy of activity.

Thus, the present invention is directed to a method for quantifying the biological or pharmacological activity of a test material by exposing a mammalian cell to the test material and assessing whether structural changes are induced in proteins present the mammalian cell. According to the present invention, any method used to study post-translational changes in cellular proteins can be used to assess whether structural changes have occurred in cellular proteins in response to a test material. For example, such structural changes include protein-protein interactions and protein phosphorylation.

In one embodiment, the present invention is directed to a method for determining whether a test material has biological activity which includes, incubating the test material with cultured mammalian cells to produce tested mammalian cells, lysing the tested mammalian cells, and comparing the pattern of phosphorylated proteins in those tested mammalian cells to the pattern of phosphorylated proteins in control cells. The control cells are the same cultured mammalian cells which have not been exposed to the test material; similarly, the control cells may be the cultured mammalian cells which are in a quiescent, or non-dividing condition.

In a further embodiment, the pattern of phosphorylated proteins in the tested mammalian cells may be compared to the pattern of phosphorylated proteins in positive control cells. Such positive control cells are the cultured mammalian cells which have been exposed to a known beneficial and non-toxic compound, an FDA approved drug or a beneficial plant or herbal extract of proven efficacy. Identification of such positive control cells is well within the ken of one of skill in the art.

The present invention is also directed to a method for determining whether a test material has biological activity which includes, incubating the test material with cultured mammalian cells to produce tested mammalian cells, lysing the tested mammalian cells to produce a mixture of cellular proteins, electrophoretically-separating the cellular proteins, reacting the cellular proteins with a monoclonal antibody directed against a phosphorylated amino acid and comparing the pattern of phosphorylated proteins in the tested mammalian cells to the pattern of phosphorylated proteins in control cells. Again, the control cells are the same cultured mammalian cells which have not been exposed to the test material. The pattern of phosphorylated proteins in these tested mammalian cells may also be compared to the pattern of phosphorylated proteins in positive control cells which have been exposed to a beneficial and non-toxic compound, an FDA approved drug or a beneficial plant or herbal extract of proven efficacy.

According to the present invention, test materials may be any compound or mixture of compounds. Thus, the present methods can be used to assess the biological activity of herbs, mixtures of herbs, herbal extracts, plant extracts, animal extracts, natural or synthetic compounds, mixtures of molecules or combinations thereof. The test material may be a purified compound but the present methods have particular utility for assessing the biological or pharmacological activity of extracts or mixtures of compounds where the active constituent or constituents have not been identified. This method thus permits the formulation of nutritional supplements and pharmacological preparations with consistent biological/pharmacological activity without the need to identify any of the chemical constituents responsible for the biological or pharmacological response.

The activity of the test material is tested by contacting that test material with cultured mammalian cells and incubating the test material with cultured mammalian cells to produce tested mammalian cells. According to the present invention, any primary or immortalized cell line may be used for this purpose. As used herein primary cell lines include cancerous and non-cancerous cells derived from any mammalian tissue specimen, for example, from mesangial, embryonic, brain, lung, breast, uterine, cervical, ovarian, prostate, adrenal cortex, skin, blood, brain, bladder, gastrointestinal, colon and related tissues. Immortalized mammalian cell lines which can be used in the present methods include human LNCaP prostate (CRL-1740), human HeLa, colon 201, neuroblastoma, retinoblastoma and KB cell lines, mouse 3T3, L and MPC cell lines, hamster CHO and BHK 21 cell lines, a monkey BSC cell line and other cell types. Immortalized mammalian cell lines may be obtained from recognized cell repositories, for example, the American Type Culture Collection.

The nature and extent of structural changes induced in the cellular proteins of mammalian cells tested by exposure to a test material may be determined by any procedure available to one of skill in the art. For example, to identify the types of proteins which may have undergone structural changes, a cell lysate of a tested population of mammalian cells can be separated under either denaturing or non-denaturing conditions. Non-denaturing conditions are used for observing protein-protein interactions. Denaturing conditions facilitate reproducible identification of individual protein species and are preferred when identifying changes in the type and amount of protein phosphorylation. Separation of both protein-protein complexes and individual proteins may be accomplished by any available chromatographic or electrophoretic procedure. For example, cellular proteins can be separated by size and/or charge using gel exclusion, ion chromatographic, reverse phase, electrophoretic or other procedures. See, e.g., Sambrook et al. MOLECULAR CLONING: A LABORATORY MANUAL, Vols. 1–3, (Cold Spring Harbor Press, NY, 1989). Such procedures are well-known, and one of skill in the art can readily adapt them for use in the present invention.

After separation, the cellular proteins which may have undergone structural changes can be visualized by any procedure available in the art. Procedures and reagents for visualizing protein are well known in the art and include, for example, staining with dyes that bind to proteins and reacting the proteins with antibodies that have a covalently attached reporter molecule. Phosphorylated proteins can be visualized by reacting the cellular proteins with monoclonal antibodies directed against the phosphorylated serine, threonine or tyrosine amino acids that are present in the proteins. For example, monoclonal antibodies useful for isolating and identifying phosphotyrosine-containing proteins are described in U.S. Pat. No. 4,543,439 to Frackelton et al. (issued Sep. 24, 1985), and Schieven et al., *Lineage-specific Induction of B Cell Apoptosis and Altered Signal Transduction by Phosphotyrosine Phosphatase Inhibitor Bis (maltolato)oxovanadium (IV)*, 270 J. BIOL. CHEM. 20824 (1995). The procedures and reagents provided in these references can readily be adapted by one of skill in the art to practice the methods of the present invention.

Antibodies used for visualizing cellular proteins can be labeled by any procedure known in the art, for example by incorporation of nucleotides linked to a "reporter molecule".

A "reporter molecule", as used herein, is a molecule which provides an analytically identifiable signal allowing one of skill in the art to identify when an antibody has bound to protein that it is directed against. Detection may be either qualitative or quantitative. Commonly used reporter molecules include fluorophores, enzymes, biotin, chemiluminescent molecules, bioluminescent molecules, digoxigenin, avidin, streptavidin or radioisotopes. Commonly used enzymes include horseradish peroxidase, alkaline phosphatase, glucose oxidase and β-galactosidase, among others. The substrates to be used with these enzymes are generally chosen for the production, upon hydrolysis by the corresponding enzyme, of a detectable color change. For example, p-nitrophenyl phosphate is suitable for use with alkaline phosphatase reporter molecules; for horseradish peroxidase, 1,2-phenylenediamine, 5-aminosalicylic acid or toluidine are commonly used. Incorporation of a reporter molecule onto an antibody can be by any method known to the skilled artisan.

After separation and visualizing the proteins, the amount of each protein species may be assessed by readily available procedures. For example, the proteins may be electrophoretically separated on a polyacrylamide gel, and after staining the separated proteins, the relative amount of each protein can be quantified by assessing its optical density.

A further aspect of this invention provides pharmaceutical compositions and nutritional supplements containing a compound, mixture of compounds or extract which was identified by the present methods as having biological or pharmacological activity. In particular, the subject compounds, mixture of compounds and extracts are provided in a therapeutically effective amount of about 0.1 $\mu$g to about 100 mg per kg of body weight per day, and preferably of about 0.1 $\mu$g to about 10 mg per kg of body weight per day, as needed to provide the pharmacological or biological activity. Dosages can be readily determined by one of ordinary skill in the art and formulated into the subject pharmaceutical compositions.

The present pharmacological compositions and nutritional supplements may be formulated with a pharmaceutically acceptable carrier. As used herein, "pharmaceutically acceptable carrier" includes any and all available solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The present pharmaceutical compositions and nutritional supplements can be administered by topical, oral or parenteral administration, for example, by intravenous, intramuscular, intraperitoneal subcutaneous or intradermal route. The subject compositions and supplements may be incorporated into a cream, solution or suspension for topical administration. For oral administration, the subject compositions and supplements may be protected by enclosure in a gelatin capsule or compressed into a tablet.

The following prophetic examples illustrate specific embodiments of the present invention.

EXAMPLE 1

Saw Palmetto (Serenoa repens) May Alter Phosphotyrosyl Protein Expression in Human LNCaP Prostate Cells Summary This example prophetically illustrates that an extract of saw palmetto produces changes in the pattern of phosphotyrosyl protein expression of rapidly growing human prostate cells. The present invention predicts that nondividing cells have few phosphorylated protein species, whereas dividing cells have several phosphorylated protein species. Moreover, according to the present invention, extracts of the saw palmetto plant may eliminate the phosphotyrosyl protein expression which may be observed in dividing cells. Further according to the present invention, the potency of saw palmetto extracts may be calculated by observing a dose-related decrease in tyrosylphosphorylation of proteins expressed in dividing cells. This can be done even though the identity and mechanism of action of the active component(s) in the complex mixture of the saw palmetto extract is unknown.

Methods

Chemicals: Anti-phosphotyrosine antibodies may be purchased from Upstate Biotechnology (Lake Placid, N.Y.). Saw palmetto (Serenoa repens) extract may be obtained from Ashland Nutritional (Irvine Calif.). All other chemicals may be purchased from Sigma Chemical Company (St. Louis, Mo.) and are the highest purity commercially available.

Human Prostate Cell Line: The LNCaP prostate cell line (CRL-1740) is useful as a model for prostate hyperplasia and may be obtained from the American Type Culture Collection (Bethesda, Md.). LNCaP cells were originally isolated from a 50-year old, Caucasian male and are characteristic of prostatic carcinoma. They are androgen and estrogen responsive, produce prostate specific antigen (PSA), and prostatic acid phosphatase in culture.

Cell Plating: LNCaP cells may be propagated as monolayers according to the instructions of the supplier. For experiments, cells may be plated at a density of $1\times10^5$ cells per mL in 100 mm plates, 20 mL per plate, 3 plates per treatment. After 24 hours, the Serenoa repens extracts may be added in 10 $\mu$L dimethylsulfoxide (DMSO) to achieve a final concentration of 0, 5, 10, 50, or 100 $\mu$g/mL.

On day three, a subset of control LNCaP cells is synchronized to $G_o$ by reducing the serum concentration of the medium to 0.5%. These cells are termed quiescent, resting or unstimulated LNCaP cells.

After a four-day incubation period with the test materials, the test LNCaP cells may be collected by washing plates three times with ice-cold phosphate-buffered saline, pH 7.4 (PBS) over ice, removed by scraping, pelleted by centrifugation at 4° C. The cell pellet may be lysed for 20 min. in 20 mM Tris buffer (pH 8.0) with 137 mM NaCl, 10% glycerol, 1% Nonidet P-40, 1 mM phenylmethylsulfonyl fluoride, 0.15 units/mL aprotonin, and 1 mM sodium orthovanadate while on wet ice. Cell lysates are collected after centrifugation at 30,000 rpm at 4° C. for 10 minutes to separate cellular debris from lysates.

Gel Electrophoresis: Sodium dodecyl sulfate polyacrylamide gel electrophoresis (PAGE) is performed using 10% polyacrylamide gels, as described by Laemmli, U.K. and Favre, M., 80 Journal of Molecular Biology 575–99 (1973), with the modification that the cell lysates (100 $\mu$g protein/lane) are heated at 100° C. for three minutes.

Immunoblotting: The immunoblotting is performed as described by Towbin et al., 76 Proc. Natl. Acad. Sci. USA 4350 (1979), however, a Milliblot SDE electroblot apparatus (Millipore, Bedford, Mass.), is used to transfer proteins from the polyacrylamide gels to an IMMOBILON® membrane filter. Complete transfers are accomplished in 25–30 minutes at 500 mA. Membranes used for blotting are blocked by incubating in TBS (Tris buffered saline, 50 mM Tris, 150 mM NaCl, pH 7.5) containing 5% nonfat dry milk for 30 minutes at room temperature. Phosphotyrosylproteins are visualized by incubation of the blots with the anti-phosphotyrosine antibody in TBST (0.05% Tween 20 in TBS) for two hours and then a second incubation at room temperature with alkaline phosphatase-conjugated secondary antibody diluted 1:1000 in TBST for two hours. The enzymatic reaction is developed for 15 minutes. Molecular weights of immuno-stained proteins are estimated by adding molecular weight standards to reference lanes and staining the membrane filters with amido black 10B.

Blots are translated into TIFF-formatted files with a Microtech 600GS scanner and quantified using Scan Analysis (BIOSOFT™, Cambridge, UK). Summary scans are then printed and peak heights are measured directly from figure. One density unit (Du) is defined as one mm of the resulting peak height.

Protein Determination: Spectrophotometric determination of protein concentration is determined with bicinchoninic acid as reported by Smith, et al. Measurement of protein using bicinchoninic acid. 150 ANAL. BIOCHEM. 76–85 (1985).

Statistical Analysis: Dose responses are defined as three or more consecutive doses resulting in a consistent, reproducible appearance or disappearance of a phosphotyrosyl-protein in the immunoblot. The percent of response relative to the positive or negative controls is determined for each dose and this variable is transformed into probits for regression analysis; a log-normal distribution is assumed. Median effective concentrations are determined using Sigma Plot (Jandel Scientific, San Rafael, Calif.).

Results

Figure 3:
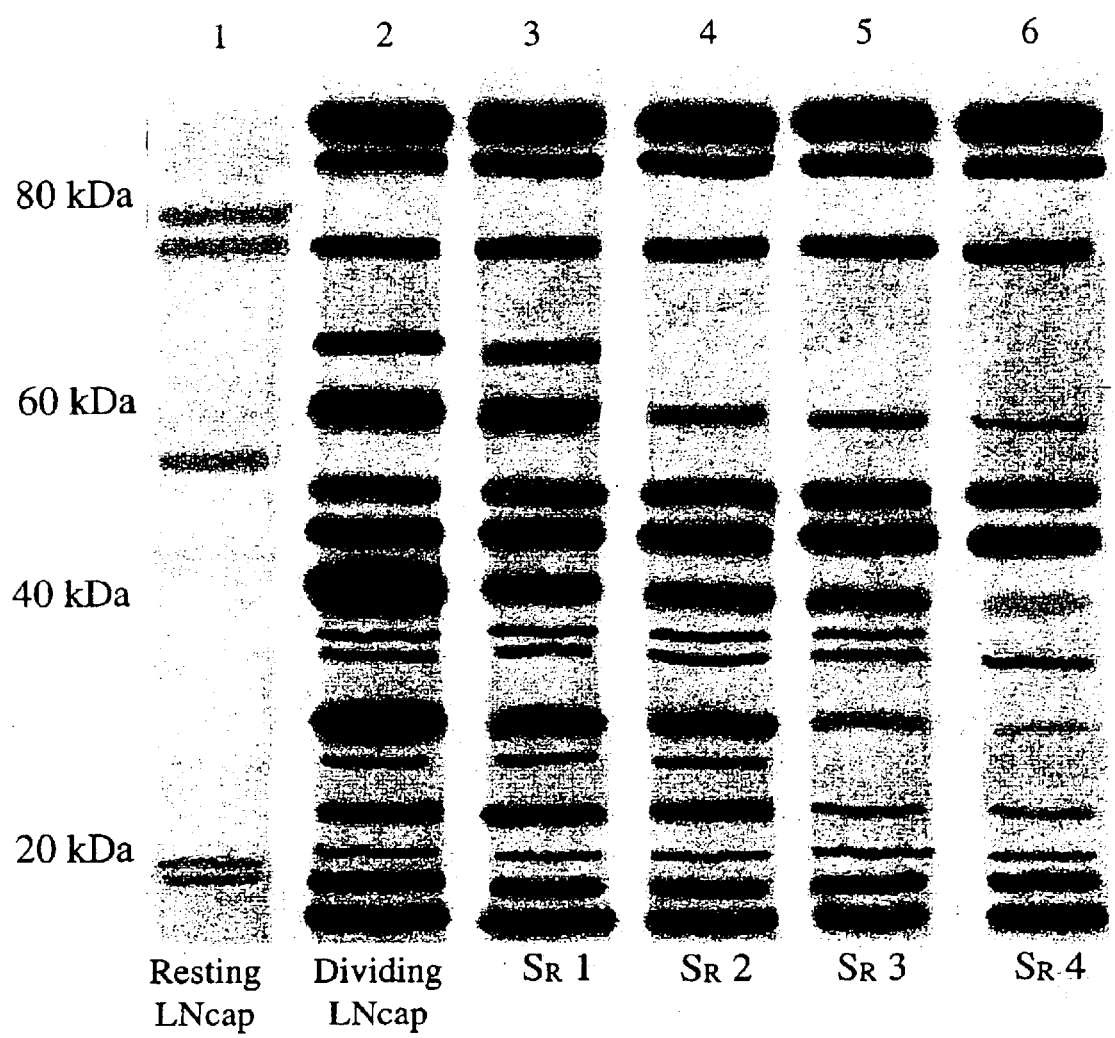
FIG. 3 provides a hypothetical protein blot to illustrate the types of dose-related changes in phosphotyrosylprotein expression that may occur in LNCaP prostate cells treated with increasing amounts of a hexane extract of Serenoa repens (saw palmetto). Lane 1 hypothetically illustrates that five lightly-staining phosphoproteins may be observed in the molecular weight range of 15 to 90 kDa in resting LNCaP cells treated only with a carrier, such as dimethylsulfoxide. Lane 2 hypothetically illustrates that sixteen phosphoproteins of various staining intensities and thicknesses may be observed in the same molecular weight range for dividing controls treated only with a carrier such as dimethylsulfoxide. Of these sixteen bands, seven may hypothetically decrease in staining intensity in relationship to increasing concentration of the S. repens extract. Thus, lanes 3, 4, 5 and 6 hypothetically represent phosphoproteins from rapidly growing LNCaP cells that are treated with increasing amounts of S. repens extract, for example, 5, 10, 50 or 100 µg, respectively. The molecular weights of these proteins may, for example, be 25, 28, 30, 36, 40, 60 and 65 kDa. A certain number of bands, for example, three bands at 25, 36 and 65 kDa, may hypothetically disappear entirely when cells are treated with increasing amounts of S. repens extract, for example, at concentrations of 50, 100 and 10 µg/mL, respectively. The dark, wide band at 40 kDa is predicted to be the most sensitive to the effects of the S. repens extract. At 5 µg S. repens extract/mL, the band may be reduced by, for example, over 60% in intensity. Continued decreases in intensity of staining may occur with increasing doses through the 100 µg/mL concentration. Given these hypothetical results, an approximate median effective concentration for the decrease in phosphotyrosylprotein at 40 kDa, would be 2.3 µg/mL.

Five, lightly staining discrete bands, representing phosphotyrosyl proteins in the molecular weight range of 15 to 90 kDa, are observed in resting, control LNCaP cells (FIG. 3). In dividing LNCaP cells sixteen bands of various staining intensities and thicknesses may be observed in the same molecular weight range. Of these sixteen bands, several may decrease in staining intensity in relationship to increasing concentration of the *S. repens* extract, for example, the proteins at 25, 28, 30, 36, 40, 60 and 65 kDa in lanes 4–6 of FIG. 3. Several bands may disappear completely, for example, the three proteins at 25, 36 and 65 kDa, which are depicted as disappearing entirely at *S. repens* extract concentrations of 50, 100 and 10 µg/mL, respectively. A dark, wide band at 40 kDa is predicted to be most sensitive to the effects of *S. repens*. For example, at 5 µg *S. repens* extract/mL, the intensity of the 40 kDa phosphoprotein band is depicted as being reduced by over 60%. Continued decreases in intensity of staining may occur with increasing dose through the 100 µg/mL concentration. An approximate median effective concentration for the decrease in phosphotyrosylprotein at 40 kDa is predicted to be 2.3 µg/mL.

Extensive changes in phosphotyrosyl protein expression in stimulated LNCaP prostate cells by the hexane extract of *S. repens* will suggest that this extract can physiologically interfere with intracellular signaling pathways. The pattern of phosphotyrosyl protein expression in clinically successful extracts may be used as a standard for identifying additional batches of extract, thereby insuring bioequivalence.

This example therefore illustrates the types of phosphorylation signaling events that a clinically successful, complex botanical mixture may produce in a single cell type. Moreover, this example suggests that these signaling events may be highly reproducible. Accordingly, a control botanical extract with a consistent biological activity can be produced and, using the procedure described in this example, new batches of extract with similar activity can be identified through comparison of phosphotyrosylprotein expression patterns. This can be accomplished without knowledge of the active ingredients in the extract or their mechanism(s) of action.

EXAMPLE 2

Alteration of Phosphotyrosyl Protein Expression of Human LNCaP Prostate Cells by an Extract of Saw Palmetto or Finasteride Summary This example hypothetically compares the phosphotyrosyl protein expression patterns of benign prostate hyperplasia cells exposed to either a purified, FDA-approved drug or a plant extract like saw palmetto. Finasteride is an FDA approved drug used for the treatment of benign prostate hyperplasia. According to the present invention, the relative potency of saw palmetto extracts may be assessed in comparison to finasteride through observation of a dose-responsive decrease or increase in tyrosylphosphorylation of a given protein species. Moreover, according to the present invention, the biological activity of a complex mixture like a saw palmetto extract may be determined without the need to separate the components of the mixture, even though the mechanism of action of the biologically active component(s) of the mixture is unknown.

Methods

Chemicals: Anti-phosphotyrosine antibodies can be purchased from Upstate Biotechnology (Lake Placid, N.Y.). Saw palmetto extract can be obtained from Ashland Nutritional (Irvine Calif.). Finasteride (F 1293) and all other chemicals can be purchased from Sigma Chemical Co. (St. Louis, Mo.) and are the highest purity commercially available.

Human Prostate Cell Line: The LNCaP prostate cell line (CRL-1740) is useful as a model for prostate hyperplasia as described in Example 1.

Cell Plating: LNCaP cells are propagated according to the instructions described in Example 1. After 24 hours, the *Serenoa repens* extracts are added in 10 µL DMSO to achieve final concentrations of 0, 10, 50, or 100 µg/mL. The finasteride positive control is tested at a single concentration of 0.05 µg/mL and is also added in 10 µL DMSO. This finasteride concentration is chosen as it represents steady-state peak concentrations observed in prostatic tissue in human clinical trails.

All other methods and procedures are as described in Example 1.

Results

Figure 4:
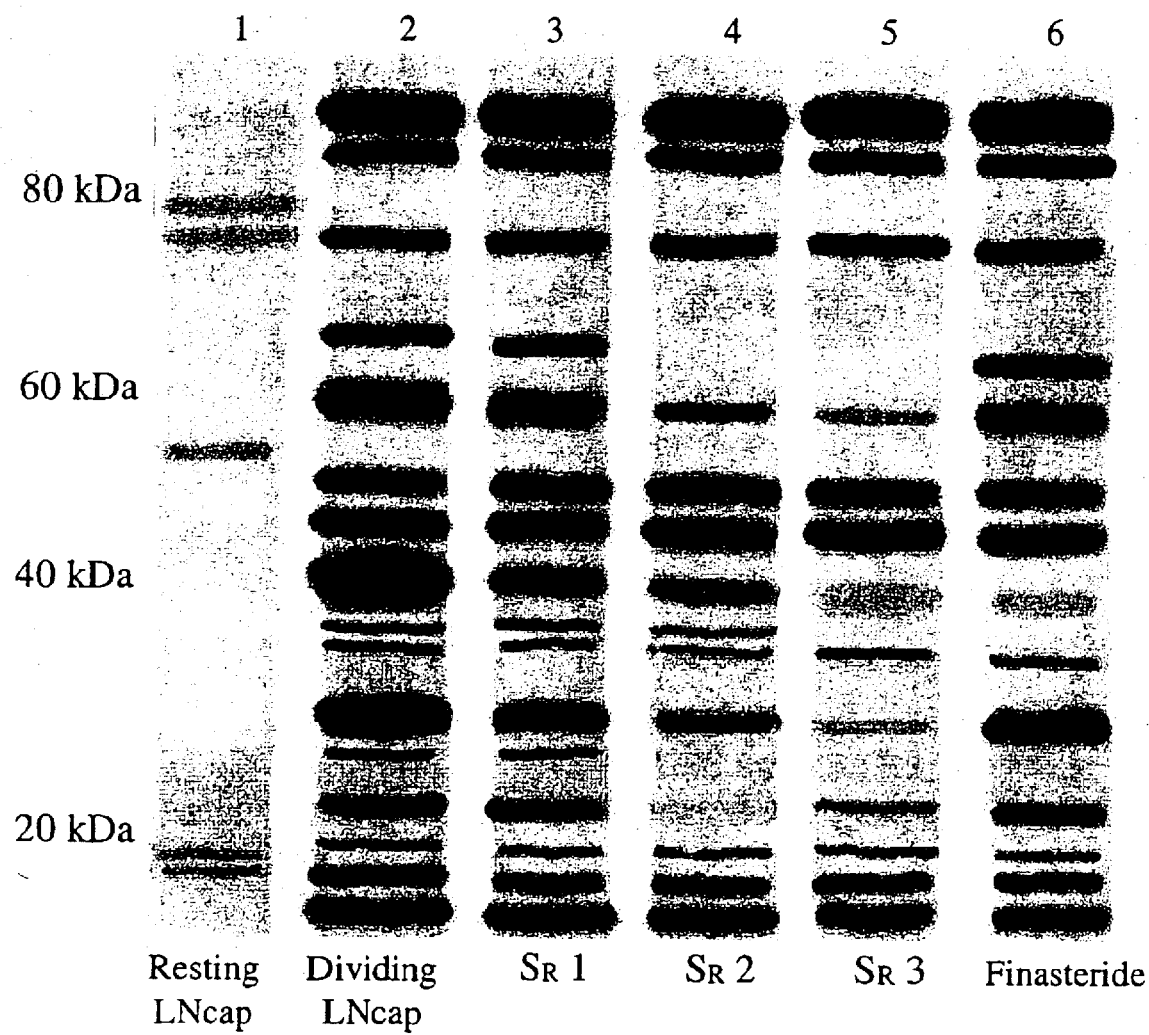
FIG. 4 provides a hypothetical protein blot to illustrate the types of dose-related changes in phosphotyrosylprotein expression that may occur in LNCaP prostate cells treated either with increasing amounts of a hexane extract of Serenoa repens (saw palmetto), or with be observed in the molecular weight range of 15 to 90 kDa in resting LNCaP cells treated only with a carrier, such as dimethylsulfoxide. Lane 2 hypothetically illustrates that sixteen phosphoproteins of various staining intensities and thicknesses may be observed in the same molecular weight range for dividing controls treated only with a carrier such as dimethylsulfoxide. Lanes 3, 4, 5 and 6 hypothetically represent phosphoproteins from rapidly growing LNCaP cells that are treated with increasing amounts of S. repens extract, for example, 5, 10, 50 or 100 g, respectively. As described above for FIG. 3, several bands observed in dividing LNCaP cells may disappear when growing LNCaP cells are treated with increasing amounts of treated with S. repens extract, for example, 10, 50 or 100 µg, respectively. Lanes 6 illustrates the hypothetical phosphoproteins observed in cells treated with a known compound, finasteride. Finasteride may affect the expression of three phosphotyrosyl proteins migrating, for example, at 28, 36, and 40 kDa. All three of these proteins may also be affected by the hexane extract of saw palmetto. However, additional phosphoproteins may be affected by the saw palmetto extract which are not affected by finasteride. Three bands, representing molecular weights of 25, 30 and 65 kDa, may hypothetically disappear entirely at higher saw palmetto extract concentrations (lanes 4 and 5) but remain visible in cells treated with finasteride (lane 6).

Five, lightly staining discrete bands, representing phosphotyrosyl proteins in the molecular weight range of 15 to 90 kDa, are observed in resting, control LNCaP cells (FIG. 4, lane 1). In dividing LNCaP cells, sixteen bands of various staining intensities and thicknesses may be observed in the same molecular weight range. Of these sixteen bands, several may decrease in staining intensity in relationship to increasing concentration of the *S. repens* extract, for example, the proteins at 25, 28, 30, 36, 40, 60 and 65 kDa in lanes 3–5 of FIG. 4. Some bands may disappear completely, for example, the two proteins at 25 and 36 kDa, which are depicted as disappearing entirely at *S. repens* extract concentrations of 50 and 100 µg/mL.

A dark, wide band at 40 kDa is predicted to be most sensitive to the effects of *S. repens*. For example, at 10 µg *S. repens* extract/mL, the intensity of the 40 kDa phosphoprotein band is depicted as being reduced by over 60%. An approximate median effective concentration for the decrease in phosphotyrosylprotein at 40 kDa is predicted to be 2.3 µg/mL.

Finasteride may influence the expression of some of the same phosphotyrosylproteins as the *S. repens* extract. For example, in lane 6 of FIG. 4, finasteride is shown to affect the expression of the 40 kDa phosphoprotein and two other phosphotyrosyl proteins migrating at 28 and 36 kDa. For illustrative purposes, tyrosylphosphorylation of the 28 and 36 kDa proteins is shown to be completely eliminated and the 40 kDa band is shown to be barely visible at the 0.05 µg/mL concentration of finasteride. Using these prophetic data to quantify the decreased expression of the 40 kDa phosphotyrosyl protein, finasteride is approximately 1000 times more potent than the *S. repens* extract in inhibiting the tyrosylphosphorylation of this protein.

Interpretation

As illustrated by this example, a hexane extract of saw palmetto may be less potent than the known drug finasteride for down-regulating the expression of certain phosphoproteins, for example, the 40 kDa phosphotyrosyl-protein. However, as illustrated, the saw palmetto extract may exhibits a wider range of down-regulation than the FDA-approved drug because it effects the expression of a wider number of phosphoproteins. According to the present invention, this wider range of regulation may translate into a similar, or even greater, clinical efficacy.

EXAMPLE 3

Differential Alterations in Phosphotyrosyl Protein Expression in Stimulated Human LNCaP Prostate Cells Treated with Beta-sitosterol or an Extract of *Serenoa repens*

Summary

This example hypothetically illustrates that a whole extract of saw palmetto provides a broader range of changes in the pattern of phosphotyrosyl protein expression in dividing human prostate cells than that produced by a single constituent of the extract, beta-sitosterol. According to the present invention, beta-sitosterol induces the expression of only some of the phosphotyrosyl proteins induced by the whole extract of saw palmetto. Moreover, very high concentrations of beta-sitosterol are predicted to be required to provide efficacy in patients. If this is so, synergy may occur between beta-sitosterol and other unidentified constituents in the saw palmetto extract. Thus, according to the present invention, a whole plant extract, which consists of a complex mixture of molecules, may have greater efficacy than a single component of that extract. Moreover, the present methods allow identification of a new biologically active complex mixture without first identifying the active ingredients, or their mechanism of action, in that mixture. Similarly, the present methods permit identification of which components may contribute to the biological activity of a complex mixture.

Methods

Chemicals: Anti-phosphotyrosine antibodies can be purchased from Upstate Biotechnology (Lake Placid, N.Y.). Saw palmetto extract can be obtained from Ashland Nutritional (Irvine Calif.). Beta-sitosterol and all other chemicals can be purchased from Sigma (St. Louis, Mo.) and are the highest purity commercially available.

Human Prostate Cell Line: The LNCaP prostate cell line (CRL-1740) is useful as a model for prostate hyperplasia as described in Example 1.

Cell Plating: The LNCaP cells are propagated according to the instructions described in Example 1. After 24 hours, the beta-sitosterol is added in 10 $\mu$L DMSO to achieve final concentrations of 5, 10 or 50 $\mu$g/mL. A hexane extract of *Serenoa repens* is added in 10 $\mu$L DMSO to achieve a final concentration of 100 $\mu$g/mL.

All other methods and procedures are as described in Example 1.

Results

Figure 5:
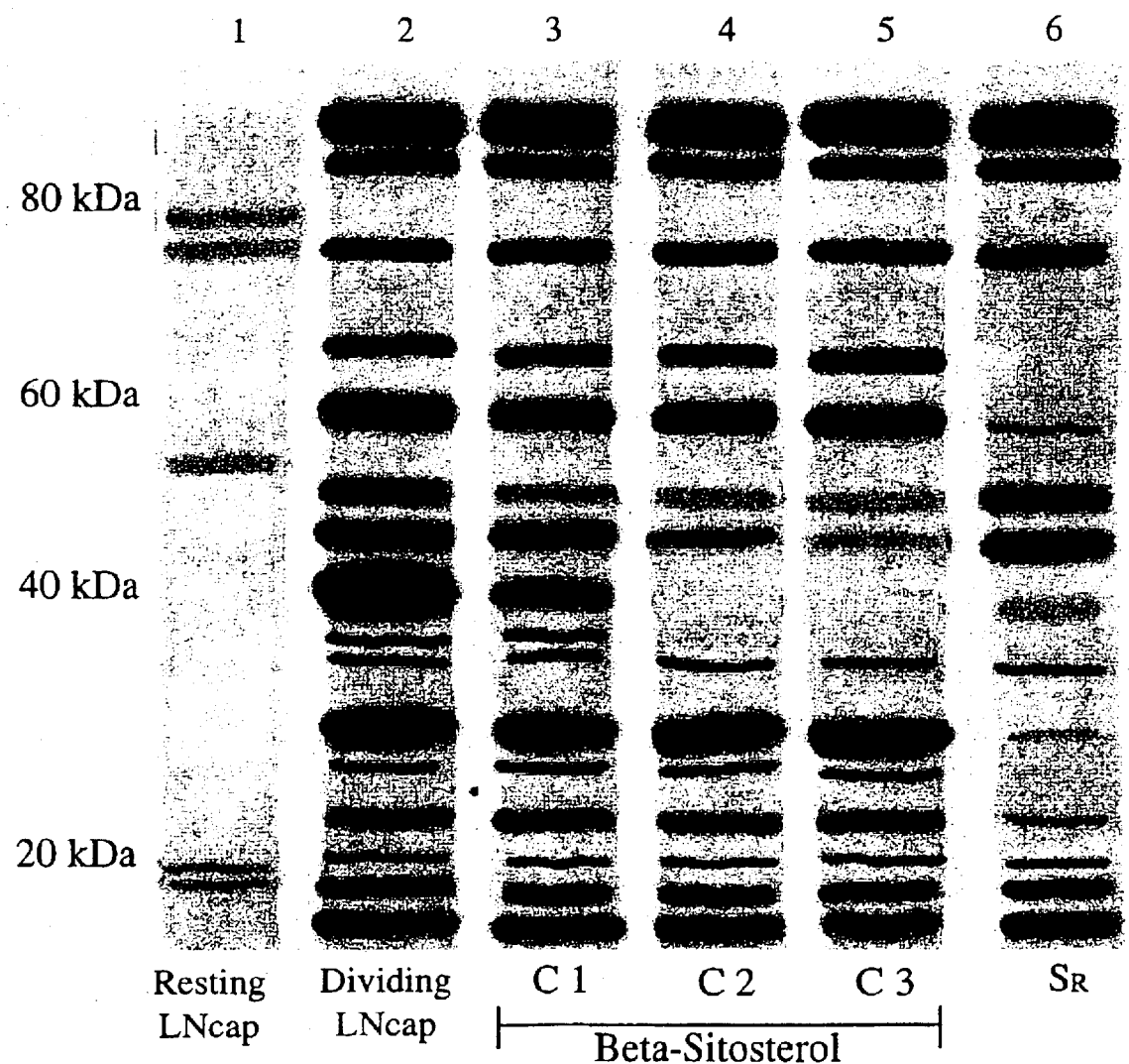
FIG. 5 provides a hypothetical protein blot to illustrate the types of dose-related changes in phosphotyrosylprotein expression that may occur in LNCaP prostate cells treated either with increasing amounts beta-sitosterol compared to such cells treated with a hexane extract of *Serenoa repens* (saw palmetto). Lanes 1 hypothetically illustrates that five lightly-staining phosphoproteins may be observed in the molecular weight range of 15 to 90 kDa in resting LNCaP cells treated only with a carrier, such as dimethylsulfoxide. Lanes 2 hypothetically illustrates that sixteen phosphoproteins of various staining intensities and thicknesses may be observed in the same molecular weight range for dividing controls treated only with a carrier such as dimethylsulfoxide. Lanes 3, 4 and 5 hypothetically represent phosphoproteins from rapidly growing LNCaP cells that are treated with increasing amounts of beta-sitosterol, for example, 5, 10 and 50 μg beta-sitosterol/mL. Lanes 6 hypothetically represents the phosphoproteins observed after treatment with 100 μg *S. repens* extract/mL for four days. In dividing LNCaP cells, sixteen bands of various staining intensities and thicknesses are hypothetically observed in the 15 to 90 kDa molecular weight range (lane 2). Of these sixteen bands, four hypothetically decrease in staining intensity when the cells are incubated with beta-sitosterol, for example, those at 36, 40, 45 and 50 kDa (lanes 3, 4 and 5). However, seven bands hypothetically decrease in staining intensity when the cells are incubated with the hexane extract of *S. repens* (lane 6), for example, those at 25, 28, 30, 36, 40, 60 and 65 kDa. The bands at 36 and 40 kDa may similarly be affected by beta-sitosterol and the hexane extract of *S. repens*. Both of these 36 and 40 kDa phosphotyrosylproteins are hypothetically diminished or disappear entirely at higher concentrations of beta-sitosterol and the hexane extract of *S. repens*.

Five, lightly staining discrete bands, representing phosphotyrosyl proteins in the molecular weight range of 15 to 90 kDa, are observed in resting, control LNCaP cells (FIG. 5, lane 1). In dividing LNCaP cells, sixteen bands of various staining intensities and thicknesses may be observed in the same molecular weight range (FIG. 5, lane 6). Of these sixteen bands, several may decrease in staining intensity as concentration of the *S. repens* extract increases, for example, the proteins at 25, 28, 30, 36, 40, 60 and 65 kDa in FIG. 5 (lane 6). Some bands may disappear completely, for example, the two proteins at 25 and 36 kDa (lane 6).

Beta-sitosterol may influence the expression of some of the same phosphotyrosylproteins as the *S. repens* extract. As hypothetically illustrated in FIG. 5, betasitosterol produces a dose-response decrease in the tyrosylphosphorylation of four proteins. Two phosphotyrosylproteins, migrating at 36 and 40 kDa, are depicted as disappearing entirely at 10 $\mu$g beta-sitosterol/mL. Two other densely staining phosphotyrosylproteins at 45 and 50 kDa are depicted as faint bands at the higher beta-sitosterol/mL concentration (50 $\mu$g). Thus, a single component of the saw palmetto extract, beta-sitosterol, may influence the expression of only a few of the phosphotyrosylproteins whose expression is influenced by the whole extract, for example, only those at 36 and 40 kDa.

Interpretation

According to the present invention, an identified active ingredient in saw palmetto extracts, beta-sitosterol, may downregulate only a few of the phosphotyrosylproteins affected by the whole saw palmetto extract such that more signaling pathways may be effected by the whole saw palmetto extract than by beta-sitosterol. Several components of the crude saw palmetto extract may therefore be necessary for optimal clinical efficacy.

EXAMPLE 4

Differential Alteration of Phosphotyrosyl Protein Expression of Human LNCaP Prostate Cells by Four Commercial Source Extracts of *Serenoa repens*

Summary

This example hypothetically illustrates that the biological activity of different commercially-available extracts of saw palmetto can be ranked by observing their respective patterns of phosphotyrosyl protein expression in cultured human prostate cells. Thus, according to the present invention, a new clinically successful batch of saw palmetto can be identified by comparing its pattern of phosphotyrosylprotein expression to the pattern of a saw palmetto extract with proven clinical efficacy. Moreover, those saw palmetto extracts having phosphotyrosylprotein patterns which are like those of a clinically successful formulation are predicted to have greater biological activity than those which are dissimilar. Thus, the present methods can permit quality control parameters to be fixed for complex mixtures of compounds, without the need for identifying the active constituents and their mechanism or action.

Methods

Chemicals: Anti-phosphotyrosine antibodies can be purchased from Upstate Biotechnology (Lake Placid, N.Y.). Saw palmetto extracts can be obtained from Ashland Nutritional (Irvine Calif., Formulation 1), Acta Pharmacal Co (Sunnyvale, Calif., Formulation 2), GCI Nutrients (Burlingame, Calif., Formulation 3), and Motherland HerbPharm, Inc. (Chino, Calif., Formulation 4). For purposes of this example, Formulation 1 is a clinically successful preparation, as demonstrated in a double-blinded, placebo control trial for the treatment of benign prostate hyperplasia. All other chemicals are purchased from Sigma (St. Louis, Mo.) and are the highest purity commercially available.

Human Prostate Cell Line: The LNCaP prostate cell line (CRL-1740) is useful as a model for prostate hyperplasia as described in Example 1.

Cell Plating: The LNCaP cells are propagated according to the instructions described in Example 1. After 24 hours, the four formulations of *Serenoa repens* extracts are added at a single concentrations of 100 $\mu$g/mL in 10 $\mu$L DMSO. Control cells are treated only with 10 $\mu$L DMSO solvent.

All other methods and procedures are as described in Example 1.

Results

Figure 6:
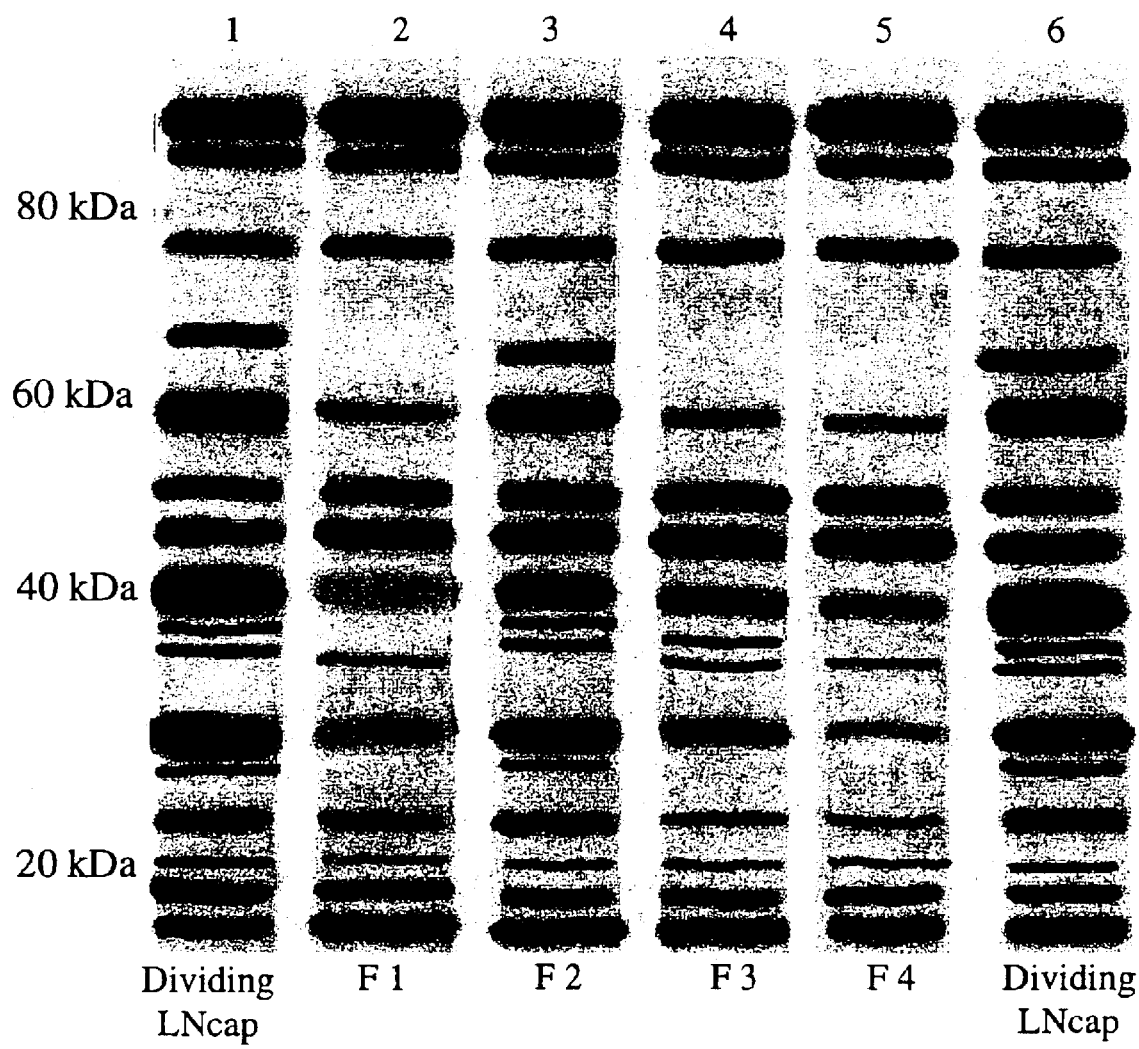
FIG. 6 provides a hypothetical protein blot to illustrate the types of changes in phosphotyrosylprotein expression that may occur in LNCaP prostate cells treated with four different extracts of *Serenoa repens* (saw palmetto). Lanes 1 and 6 hypothetically illustrate that sixteen phosphoproteins of various staining intensities and thicknesses may be observed in the 15 to 90 kDa molecular weight range for dividing LNCaP cells treated only with a carrier such as dimethylsulfoxide. Lanes 2, 3, 4 and 5 hypothetically represent phosphoproteins from rapidly growing LNCaP cells that are treated with four different commercial formulations F1, F2, F3 or F4 (for example, at 100 μg *S. repens* extract/mL for four days). Of the sixteen bands hypothetically observed in dividing LNCaP cells, seven hypothetically decrease in staining intensity when cells are treated with the *S. repens* Formulation 1 (lane 2). Formulation 1 may, for example, be selected because it has proven clinical success in double-blinded, placebo control trials of saw palmetto extract in the treatment of benign prostate hyperplasia. The molecular weights of these seven proteins are hypothetically 25, 28, 30, 36, 40, 60 and 65 kDa. Formulation 2 (lane 3) hypothetically demonstrates no downregulation of protein tyrosylphosphorylation at any of the seven molecular weights. Formulation 4 (lane 5) hypothetically produces a pattern of protein tyrosylphosphorylation identical to Formulation 1, while Formulation 3 (lane 4) hypothetically differs from Formulations 1 and 4 because a phosphotyrosylprotein band at 36 kDa is present and the intensity of staining of the 30 kDa band is slightly increased.

Sixteen bands of various staining intensities and thicknesses may be observed in dividing LNCaP cells in the molecular weight range of 15 to 90 kDa (FIG. 6 lanes 1 and 6). Of these sixteen bands, several may decrease in staining intensity when the cells are exposed to 100 μg/mL of the *S. repens* Formulation 1, for example, the proteins at 25, 28, 30, 36, 40, 60 and 65 kDa (FIG. 6 lane 2). Two bands, representing molecular weights of 25 and 36 kDa, are depicted as disappearing entirely. The phosphotyrosylprotein which is depicted as being the most sensitive to the effects of the *S. repens* extract, is a dark, wide band at 40 kDa. For purposes of this example, Formulation 1 is a clinically successful batch as shown in double-blinded, placebo control trials of saw palmetto extracts for the treatment of benign prostate hyperplasia.

In contrast to Formulation 1, Formulation 2 (lane 3) is depicted as showing no downregulation of protein tyrosylphosphorylation at any of the seven phosphoproteins affected by Formulation 1. Formulation 4 (FIG. 6 lane 5) is depicted as providing a pattern of protein tyrosylphosphorylation identical to Formulation 1, while Formulation 3 (FIG. 6 lane 4) is depicted as differing from Formulations 1 and 4 because it does not down regulate a phosphotyrosylprotein at 36 kDa and causes a slight increase in intensity of staining of the 30 kDa band.

Based upon such results, Formulation 4 will most likely produce clinical results similar to Formulation 1. Formulation 3 is very close to Formulation 1 in the pattern of protein tyrosylphosphorylation induced, but the differences may produce somewhat different clinical results. It is clear that Formulation 2 would differ considerably from Formulation 1 in clinical effectiveness. Based upon such hypothetical in vitro results, the probability of clinical success with Formulation 2 is low, but that for Formulation 4 is high.

Interpretation

This example illustrates how one may assess the biological activity of various hexane extracts of saw palmetto in vitro by observing the extent to which they can downregulate protein tyrosylphosphorylation in target cells. According to the present invention, comparison of the phosphoprotein expression pattern induced by a clinically successful extract of saw palmetto with newly isolated extracts allows potentially clinically successful extracts to be identified. Thus, the present methods permit development of quality control parameters for herbal preparations and other complex mixtures of molecules.

EXAMPLE 5

Differential Alterations in Phosphotyrosyl Protein Expression in Stimulated Human LNCaP Prostate Cells Treated with Methylcobalamine or *Serenoa repens*

Summary

This example illustrates that a hexane extract of saw palmetto may influence the phosphotyrosyl protein expression in cultured human prostate cells more broadly than a compound that has previously exhibited growth inhibitory activity in those cells, methylcobalamine. According to the present invention, saw palmetto and methylcobalamine each have a unique effect upon the stimulated, growing LNCaP cell, and agents which exhibit such unique and, different effects on patterns of protein tyrosine phosphorylation may produce synergistic effects when combined into a single formulation.

Methods

Chemicals: Anti-phosphotyrosine antibodies can be purchased from Upstate Biotechnology (Lake Placid, N.Y.). Saw palmetto extract can be obtained from Ashland Nutritional (Irvine Calif.). Methylcobalamine and all other chemicals are purchased from Sigma (St. Louis, Mo.) and are the highest purity commercially available.

Human Prostate Cell Line: The LNCaP prostate cell line (CRL-1740) is useful as a model for prostate hyperplasia as described in Example 1.

Cell Plating: The LNCaP cells are propagated as described in Example 1. After 24 hours, the methylcobalamine is added in 10 μL PBS to achieve final concentrations of 5, 50 or 500 μg/mL. A hexane extract of *Serenoa repens* is added in 10 μL DMSO to achieve a final concentration of 100 μg/mL.

All other methods and procedures are as described in Example 1.

Results

Figure 7:
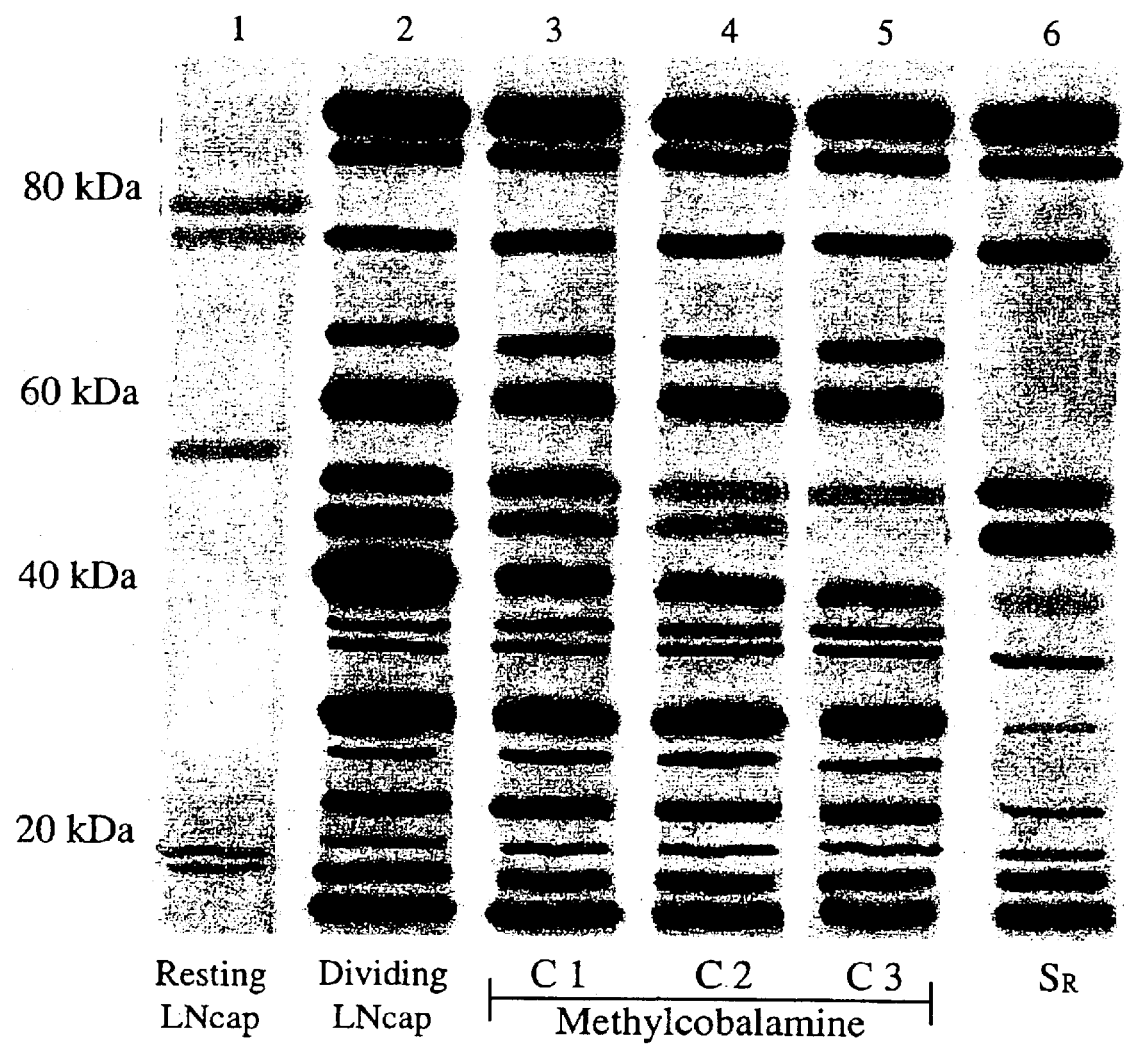
FIG. 7 provides a hypothetical protein blot to illustrate the types of dose-related changes in phosphotyrosylprotein expression that may occur in LNCaP prostate cells treated either with increasing amounts methylcobalamine or a hexane extract of *Serenoa repens* (saw palmetto). Lanes 1 hypothetically illustrates that five lightly-staining phosphoproteins may be observed in the molecular weight range of 15 to 90 kDa in resting LNCaP cells treated only with a carrier, such as dimethylsulfoxide. Lanes 2 hypothetically illustrates that sixteen phosphoproteins of various staining intensities and thicknesses may be observed in the same molecular weight range for dividing controls treated only with a carrier such as dimethylsulfoxide. Lanes 3, 4 and 5 hypothetically represent phosphoproteins from rapidly growing LNCaP cells that are treated with increasing amounts of methylcobalamine, for example, 5, 50 or 500 μg/mL methylcobalamine. Lanes 6 hypothetically represents the phosphoproteins observed after treatment with 100 μg *S. repens* extract/mL for four days. In dividing LNCaP cells, sixteen bands of various staining intensities and thicknesses are hypothetically observed in the 15 to 90 kDa molecular weight range (lane 2). Of these sixteen bands, three hypothetically decrease in staining intensity when the cells are incubated with methylcobalamine, for example, those at 40, 45 and 50 kDa (lanes 3, 4 and 5). One phosphotyrosylproteins, migrating at 45 kDa hypothetically disappears entirely at 500 μg methylcobalamine/mL. However, seven bands hypothetically decrease in staining intensity when the cells are incubated with the hexane extract of *S. repens* (lane 6), for example, those at 25, 28, 30, 36, 40, 60 and 65 kDa. Only the band at 40 kDa may thus be similarly affected by methylcobalamine and the hexane extract of *S. repens*.

Five, lightly staining discrete bands, representing phosphotyrosyl proteins in the molecular weight range of 15 to 90 kDa, are observed in resting, control LNCaP cells (FIG. 7, lane 1). In dividing LNCaP cells, sixteen bands of various staining intensities and thicknesses are observed in the same molecular weight range (lane 2). Of these sixteen bands, several may decrease in staining intensity as the concentration of the *S. repens* extract increases, for example, the proteins at 25, 28, 30, 36, 40, 60 and 65 kDa in FIG. 5 (lane 6). Some bands may disappear completely, for example, the two proteins at 25 and 36 kDa (lane 6).

Methylcobalamine may influence the expression of some of the same phosphotyrosylproteins as the *S. repens* extract. As hypothetically illustrated in FIG. 7, methylcobalamine at 5, 50 or 500 μg/mL produces a dose-response decrease in the tyrosylphosphorylation of three proteins. One phosphotyrosylprotein, migrating at 45 kDa is depicted as disappearing entirely at 500 μg methylcobalamine/mL. Two densely staining phosphotyrosylproteins at 40 and 50 kDa are depicted as faint bands even at the 500 μg methylcobalamine/mL concentration. Methylcobalamine and the hexane extract of saw palmetto similarly effect only the phosphotyrosylprotein at 40 kDa.

Interpretation

As illustrated by this example, both hexane extracts saw palmetto and methylcobalamine, a vitamin B12 analog, are thought to be capable of inhibiting the growth of LNCaP cells. The mechanisms by which these materials may carry out this function are unknown and, as illustrated in this example, are different. Thus, the phosphotyrosylproteins affected by methylcobalamine may be different than those affected by saw palmetto, for example, the expression of a phosphoprotein at 45 kDa is depicted as being affected by methylcobalamine but not by saw palmetto. Similarly, the expression of a 50 kDa phosphotyrosylprotein, is depicted as being dramatically effected by methylcobalamine, but not by the saw palmetto extract. However, the extract of saw palmetto is depicted is depicted as effecting the expression of a wide range of proteins at 25, 28, 30, 36, 60 and 65 kDa. Thus, different agents may operate via separate tyrosylphosphorylation signaling pathways.

Methylcobalamine may influence the expression of some of the same phosphotyrosylproteins as the *S. repens* extract. The effective concentration illustrated here for methylcobalamine, approximately 500 μg/mL, is higher than can be likely achieved in vivo by oral administration. However, if methylcobalamine and saw palmetto affect different tyrosylphosphorylation pathways the two can be combined to provide a wider range of effects which may allow for better clinical results at lower doses than could be used for either agent alone. According to the present invention, this information can be obtained without knowledge of the direct mechanism of action of either agent.

EXAMPLE 6

Differential Alterations in Phosphotyrosyl Protein Expression in Stimulated Human LNCaP Prostate Cells Treated with Ursolic Acid or *Serenoa repens*

Summary

This example hypothetically illustrates that a triterpene compound, ursolic acid, which has previously exhibited growth inhibitory activity in LNCaP cells, may effect the expression of phosphotyrosyl proteins differently than does a hexane extract of saw palmetto. Both ursolic acid and saw palmetto may therefore have a unique effect upon the stimulated, growing LNCaP cell. According to the present invention, the relative contribution of different agents to the general physiological state of the cell may be assessed by observing the expression of phosphotyrosyl proteins, without knowledge of the direct mechanism of action of the various agents. Both similarities and differences in the contributions of different agents to the cell's physiological state may be assessed. Moreover, agents exhibiting differing effects may produce synergistic effects when combined. Thus a combination of agents, at lower doses than any agent alone, may allow for better clinical control of cell growth than could be achieved by any one agent.

Methods

Chemicals: Anti-phosphotyrosine antibodies may be purchased from Upstate Biotechnology (Lake Placid, N.Y.). Saw palmetto extract may be obtained from Ashland Nutritional (Irvine Calif.). Ursolic acid and all other chemicals can be purchased from Sigma (St. Louis, Mo.) and are the highest purity commercially available.

Human Prostate Cell Line: The LNCaP prostate cell line (CRL-1740) is useful as a model for prostate hyperplasia as described in Example 1.

Cell Plating: The LNCaP cells are propagated as described in Example 1. After 24 hours, the ursolic acid is added in 10 $\mu$L DMSO to achieve a final concentrations of 0.5, 1 or 5 $\mu$g/mL. A hexane extract of *Serenoa repens* is added in 10 $\mu$L DMSO to achieve a final concentration of 100 $\mu$g/mL.

All other methods and procedures are as described in Example 1.

Results

Figure 8:
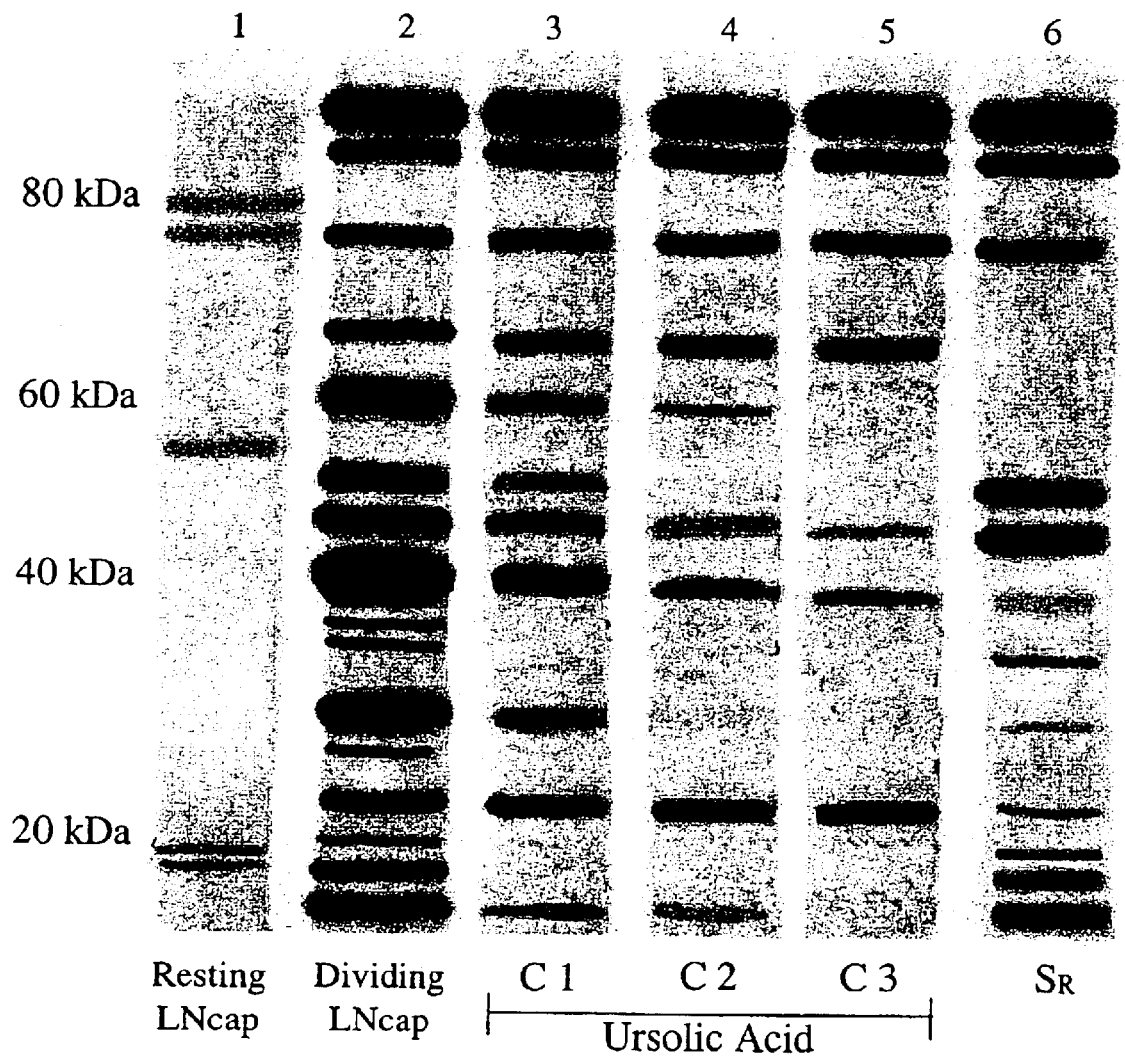
FIG. 8 provides a hypothetical protein blot to illustrate the types of dose-related changes in phosphotyrosylprotein expression that may occur in LNCaP prostate cells treated either with increasing amounts ursolic acid or a hexane extract of *Serenoa repens* (saw palmetto). Lanes 1 hypothetically illustrates that five lightly-staining phosphoproteins may be observed in the molecular weight range of 15 to 90 kDa in resting LNCaP cells treated only with a carrier, such as dimethylsulfoxide. Lanes 2 hypothetically illustrates that sixteen phosphoproteins of various staining intensities and thicknesses may be observed in the same molecular weight range for dividing controls treated only with a carrier such as dimethylsulfoxide. Lanes 3, 4 and 5 hypothetically represent phosphoproteins from rapidly growing LNCaP cells that are treated with increasing amounts of ursolic acid, for example, 5, 50 or 500 μg/mL ursolic acid. Lanes 6 hypothetically represents the phosphoproteins observed after treatment with 100 μg *S. repens* extract/mL for four days. In dividing LNCaP cells, sixteen bands of various staining intensities and thicknesses are hypothetically observed in the 15 to 90 kDa molecular weight range (lane 2). Of these sixteen bands, ten hypothetically decrease in staining intensity when the cells are incubated with ursolic acid (lanes 3, 4 and 5). Four phosphotyrosylproteins, migrating at 17, 20, 28 and 34 kDa hypothetically disappear entirely at the lowest concentration tested (for example, 0.5 μg ursolic acid/mL). At the highest concentration hypothetically tested (for example, 5 μg ursolic acid/mL), four phosphotyrosylproteins at 28, 30, 50 and 60 kDa seen in controls are no longer visible. Of the ten proteins which may be affected by ursolic acid, only the 40 and 45 kDa proteins remain at he highest concentration as thin, lightly staining bands (lane 5). Hence, ursolic acid hypothetically affects the phosphorylation of five proteins in LNCaP cells that are not effected by the saw palmetto extract. These proteins migrate, for example, at 17, 20, 34, 45, and 50 kDa. Phosphotyrosylproteins at, for example, 28, 30, 36, 40, and 60 kDa are hypothetically downregulated by both ursolic acid and saw palmetto. Conversely, proteins at 25 and 65 kDa are hypothetically downregulated by saw palmetto but not by ursolic acid.

Five, lightly staining discrete bands, representing phosphotyrosyl proteins in the molecular weight range of 15 to 90 kDa, are observed in resting, control LNCaP cells (FIG. 8, lane 1). In dividing LNCaP cells, sixteen bands of various staining intensities and thicknesses are observed in the same molecular weight range. Of these sixteen bands, several may decrease in staining intensity as the concentration of the *S. repens* extract increases, for example, the proteins at 25, 28, 30, 36, 40, 60 and 65 kDa in FIG. 5 (lane 6). Some bands may disappear completely, for example, the two proteins at 25 and 36 kDa (lane 6).

Ursolic acid may influence the expression of some of the same phosphotyrosylproteins as the *S. repens* extract. As illustrated in FIG. 8, ursolic acid at 0.5, 1 or 5 $\mu$g/mL produces a dose-response decrease in the tyrosylphosphorylation of ten proteins. Four phosphotyrosylproteins, migrating at 17, 20, 28 and 34 kDa disappear entirely at 0.5 $\mu$g ursolic acid/mL, the lowest concentration tested. At 5 $\mu$g ursolic acid/mL, the highest concentration tested, four additional phosphotyrosylproteins at 28, 30, 50 and 60 kDa are no longer visible. Of the ten proteins affected by ursolic acid, only the 40 and 45 kDa proteins remain at 5 $\mu$g/mL (lane 5) as thin, lightly staining bands.

Therefore, ursolic acid treatment of LNCaP cells may affect the expression of some of the same and some different phosphoryltyrosine proteins than are affected by saw palmetto. FIG. 8 depicts that five additional phosphoryltyrosine proteins are effected by ursolic acid that are not effected by saw palmetto, for example, proteins migrating at 17, 20, 34, 45, and 50 kDa. Phosphotyrosylproteins at 28, 30, 36, 40, and 60 kDa are depicted as being downregulated by both ursolic acid and saw palmetto. Conversely, proteins at 25 and 65 kDa are depicted as being downregulated by saw palmetto and are not affected by ursolic acid.

Interpretation

Ursolic acid is known to be an inhibitor of growth in LNCaP cells and saw palmetto is thought to be an inhibitor of growth in LNCaP cells. However, the mechanisms by which these agents carry out this function are unknown. This example suggests that those mechanisms are different. Ursolic acid effects expression of five major phosphotyrosylproteins at 17, 20, 34, 45 and 50 kDa, but these are hypothesized to not be effected by saw palmetto. The major phosphotyrosylproteins affected by saw palmetto at 25, 28, 30, 36, 40, 60 and 6 kDa, but these are though not to be effected by ursolic acid. Thus, according to the present invention, each agent affects cell growth via separate signaling pathways. If ursolic acid and saw palmetto affect different tyrosylphosphorylation pathways, those two agents can be combined to provide a single formulation that has a broader physiological effect. Such a combination of agents may permit better control of cell growth using lower concentrations of therapeutic agents than would be needed for either agent alone.

EXAMPLE 7

Differential Alterations in Phosphotyrosyl Protein Expression in Stimulated Human LNCaP Prostate Cells Treated with Lycopene or *Serenoa repens*

Summary

This example hypothetically illustrates that a lycopene, which has been shown epidermiologically to have a protective effect against benign prostate hyperplasia, may effect the expression of phosphotyrosyl proteins differently than does a hexane extract of saw palmetto.

Both lycopene and saw palmetto may therefore have a unique effect upon the stimulated, growing LNCaP cell. According to the present invention, the relative contribution of different agents to the general physiological state of the cell may be assessed by observing the expression of phosphotyrosyl proteins, without knowledge of the direct mechanism of action of the various agents. Both similarities and differences in the contributions of different agents to the cell's physiological state may be assessed. Moreover, agents exhibiting differing effects may produce synergistic effects when combined. Thus a combination of agents, at lower doses than any agent alone, may allow for better clinical control of cell growth than could be achieved by any one agent.

Methods

Chemicals: Anti-phosphotyrosine antibodies can be purchased from Upstate Biotechnology (Lake Placid, N.Y.). Saw palmetto extract can be obtained from Ashland Nutritional (Irvine Calif.). Lycopene and all other chemicals are purchased from Sigma (St. Louis, Mo.) and are the highest purity commercially available.

Human Prostate Cell Line: The LNCaP prostate cell line (CRL-1740) is useful as a model for prostate hyperplasia as described in Example 1.

Cell Plating: The LNCaP cells are propagated as described in Example 1. After 24 hours, lycopene is added at concentrations of 100, 500 or 1000 ng/mL in DMSO. A hexane extract of *Serenoa repens* is added at a concentration of 100 $\mu$g/mL in DMSO.

All other methods and procedures are as described in Example 1.

Results

Figure 9:
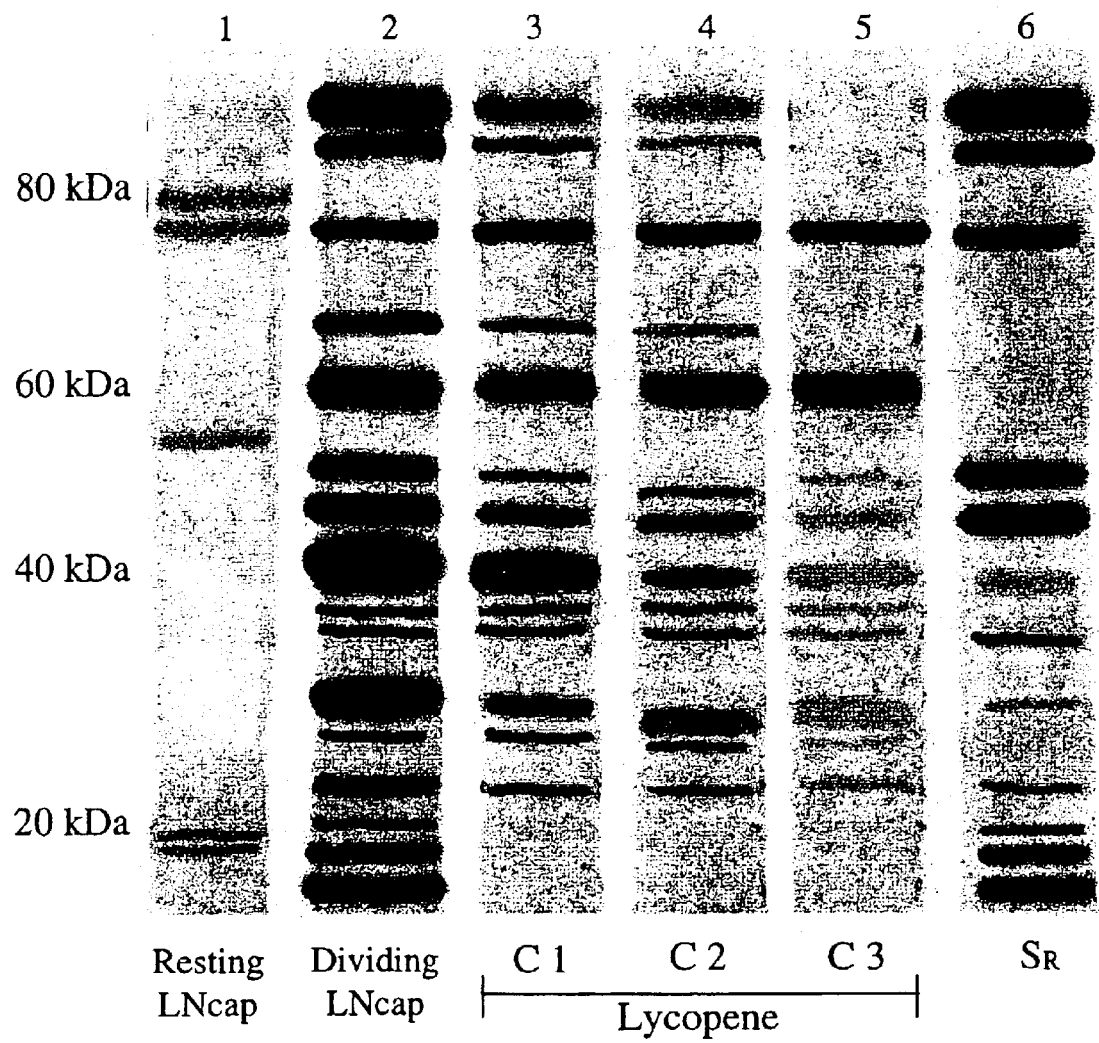
FIG. 9 provides a hypothetical protein blot to illustrate the types of dose-related changes in phosphotyrosylprotein expression that may occur in LNCaP prostate cells treated either with increasing amounts lycopene or a hexane extract of *Serenoa repens* (saw palmetto). Lanes 1 hypothetically illustrates that five lightly-staining phosphoproteins may be observed in the molecular weight range of 15 to 90 kDa in resting LNCaP cells treated only with a carrier, such as dimethylsulfoxide. Lanes 2 hypothetically illustrates that sixteen phosphoproteins of various staining intensities and thicknesses may be observed in the same molecular weight range for dividing controls treated only with a carrier such as dimethylsulfoxide. Lanes 3, 4 and 5 hypothetically represent phosphoproteins from rapidly growing LNCaP cells that are treated with increasing amounts of lycopene, for example, 100, 500 or 1000 ng/mL lycopene. Lanes 6 hypothetically represents the phosphoproteins observed after treatment with 100 μg *S. repens* extract/mL for four days. In dividing LNCaP cells, sixteen bands of various staining intensities and thicknesses are hypothetically observed in the 15 to 90 kDa molecular weight range (lane 2). Of these sixteen bands, fourteen hypothetically decrease in staining intensity when the cells are incubated with ursolic acid (lanes 3, 4 and 5). Three phosphotyrosylproteins, migrating at 15, 17, and 20 kDa hypothetically disappear entirely at the lowest concentration tested (for example, 100 ng lycopene/mL). Only six of the fourteen proteins hypothetically affected by lycopene are also hypothetically downregulated by saw palmetto. Only one protein, migrating at 60 kDa, is hypothetically downregulated by saw palmetto and is not affected by lycopene.

Five, lightly staining discrete bands, representing phosphotyrosyl proteins in the molecular weight range of 15 to 90 kDa, are observed in resting, control LNCaP cells (FIG. 9, lane 1). In dividing LNCaP cells, sixteen bands of various staining intensities and thicknesses are observed in the same molecular weight range. Of these sixteen bands, several may decrease in staining intensity as the concentration of the *S. repens* extract increases, for example, the proteins at 25, 28, 30, 36, 40, 60 and 65 kDa in FIG. 5 (lane 6). Some bands may disappear completely, for example, the two proteins at 25 and 36 kDa (lane 6).

Lycopene, may influence the expression of some of the same phosphotyrosylproteins as the *S. repens* extract. As illustrated in FIG. 9, lycopene is depicted as providing a dose-response decrease in the tyrosylphosphorylation of fourteen proteins. Three phosphotyrosylproteins, migrating at 15, 17, and 20 kDa are depicted as disappearing entirely at 100 ng lycopene/mL, the lowest concentration tested. Only six of the fourteen proteins affected by lycopene are depicted as being downregulated by saw palmetto; the eight dissimilar proteins include those migrating at 15, 17, 20, 34, 45, 50, 86 and 90 kDa. Only one protein, is migrating at 60 kDa, is depicted as being downregulated by saw palmetto but not as being affected by lycopene.

Interpretation

A hexane extract of saw palmetto and lycopene, a naturally occurring carotenoid, are known to have positive effects on prostate health. However, the mechanisms by which these agents carry out these positive effects are unknown. This example suggests that those mechanisms are different—each agent may affect cell growth via a separate cellular signaling pathway. Thus, for example, the major phosphotyrosylproteins which may be affected by lycopene are 15, 17, 20, 34, 45, 50, 86 and 90 kDa proteins. The expression of these proteins may not affected by the hexane extract of saw palmetto. According to the present invention, if lycopene and saw palmetto affect different tyrosylphosphorylation pathways, and both inhibit cell growth, a combination of the two may permit better control of cell growth inhibitor than either does alone. Moreover, lower concentrations of these agents may be used than if each agent was administered alone.

EXAMPLE 8

Synergy of *Serenoa repens*, Methylcobalamine, Ursolic Acid, and Lycopene in the Alteration of Phosphotyrosyl Protein Expression of Human LNCaP Prostate Cells Summary This example hypothetically illustrates that a combination of agents, each with a somewhat different effect upon protein tyrosine phosphorylation, when combined at individual concentrations that are not effective, produce dramatic changes in tyrosylphosphorylation and inhibit growth of cells without any toxicity. Thus, a combination of the ingredients may allow for better growth inhibitory results at lower concentrations than each agent alone. According to the present invention, this information can be obtained without knowledge of the exact mechanism(s) of action of any of the agents used to produce the combination.

Methods

Chemicals: Anti-phosphotyrosine antibodies may be purchased from Upstate Biotechnology (Lake Placid, N.Y.). Saw palmetto extract may be obtained from Ashland Nutritional (Irvine Calif.). Methylcobalamine, ursolic acid, lycopene and all other chemicals are purchased from Sigma (St. Louis, Mo.) and are the highest purity commercially available. A mixture (SrM) containing 5 µg saw palmetto extract/mg, 1 µg methylcobalamine/mg, 0.1 µg ursolic acid/mg and 25 ng lycopene/mg is used as the test material. All concentrations of individual components are selected on the basis of their individual inability to produce an effect on the protein tyrosine phosphorylation pattern of LNCaP cells in culture.

Human Prostate Cell Line: The LNCaP prostate cell line (CRL-1740) is useful as a model for prostate hyperplasia as described in Example 1.

Cell Plating: The LNCaP cells are propagated as described in Example 1. After 24 hours, SrM is added in DMSO to achieve final concentrations of 0.1, 0.5, 1.0 or 5.0 mg SrM/mL.

All other methods and procedures are as described in Example 1.

Results

Figure 10:
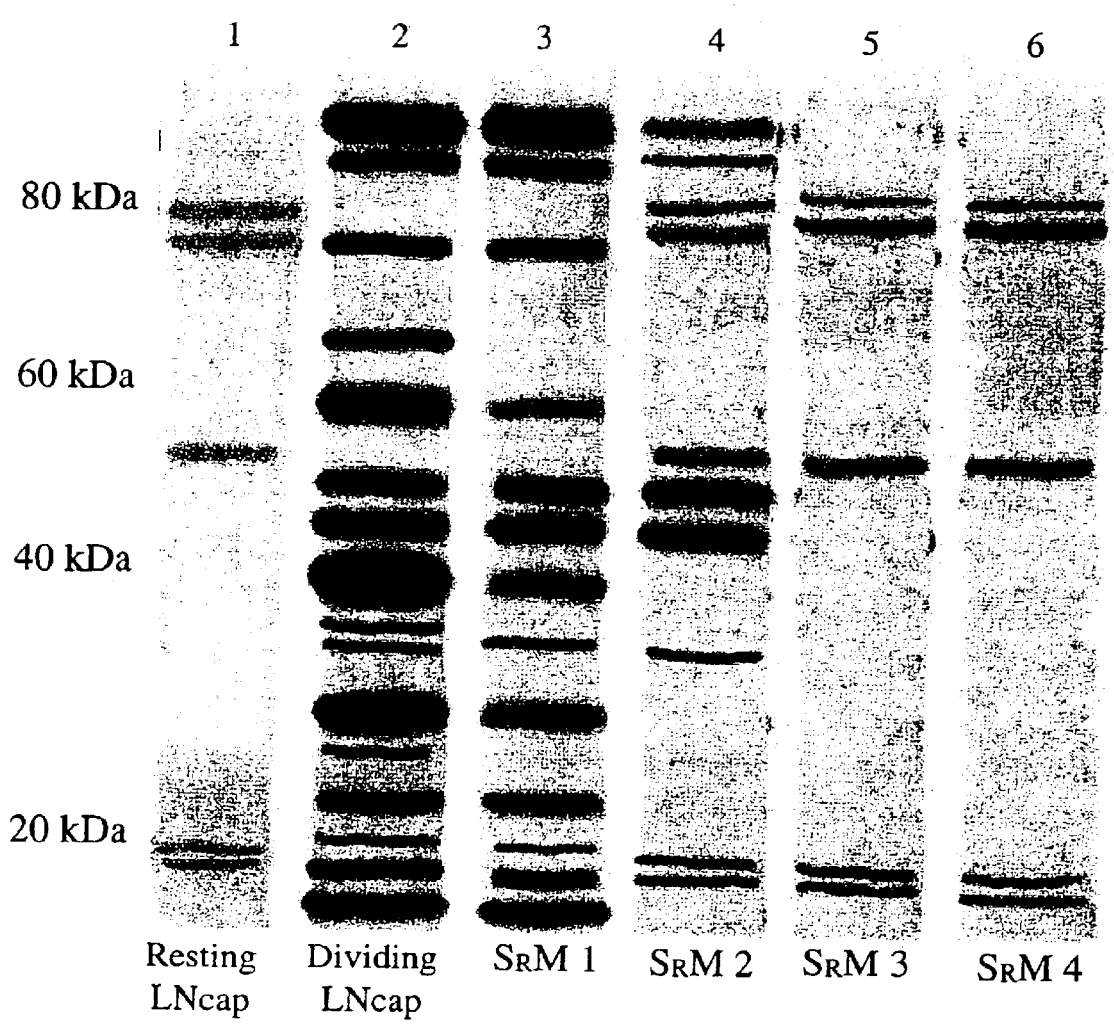
FIG. 10 provides a hypothetical protein blot to illustrate the types of dose-related changes in phosphotyrosylprotein expression that may occur in LNCaP prostate cells treated with increasing amounts of a mixture of methylcobalamine, ursolic acid, lycopene and a hexane extract of *Serenoa repens* (saw palmetto). Lanes 1 hypothetically illustrates that five lightly-staining phosphoproteins may be observed in the molecular weight range of 15 to 90 kDa in resting LNCaP cells treated only with a carrier, such as dimethylsulfoxide. Lanes 2 hypothetically illustrates that sixteen phosphoproteins of various staining intensities and thicknesses may be observed in the same molecular weight range for dividing controls treated only with a carrier such as dimethylsulfoxide. Lanes 3, 4, 5 and 6 hypothetically represent phosphoproteins from rapidly growing LNCaP cells that are treated with increasing amounts of a mixture of methylcobalamine, ursolic acid, lycopene and an *S. repens* extract. In dividing LNCaP cells, sixteen bands of various staining intensities and thicknesses are hypothetically observed in the 15 to 90 kDa molecular weight range (lane 2). With increasing concentration of the mixture of methylcobalamine, ursolic acid, lycopene and an *S. repens* extract, all bands indicative of dividing cells hypothetically disappear. At certain concentrations of the mixture, the pattern of protein tyrosylphosphorylation appears identical to the resting LNCaP cells (lanes 4, 5, 6).

Five, lightly staining discrete bands, representing phosphotyrosyl proteins in the molecular weight range of 15 to 90 kDa, are observed in resting, control LNCaP cells (FIG. 10, lane 1). In dividing LNCaP cells, sixteen bands of various staining intensities and thicknesses are observed in the same molecular weight range (lane 2). As hypothetically illustrated in FIG. 10, increasing concentration of the SrM mixture causes all bands indicative of dividing cells to disappear so that the pattern of protein tyrosylphosphorylation appears identical to the resting LNCaP cells at 1.0 and 5.0 mg SrM/mL (lanes 4, 5, 6).

Interpretation

A mixture of saw palmetto, methylcobalamine, ursolic acid and lycopene may downregulate protein tyrosine phosphorylation in stimulated LNCaP cells to a degree that is identical to nondividing cells. Moreover, concentrations below those previously demonstrated effective in the downregulation of protein tyrosine phosphorylation can hypothetically be used when the mixture is employed. Thus, according to the present invention, unrelated agents having different protein tyrosine phosphorylation patterns in dividing cells may be combined to produce a mixture with a potency greater than the sum of the individual components.

EXAMPLE 9

Alteration of Phosphotyrosyl Protein Complex Expression of Human HL60 T Cells by Extracts of *Echinacea angustifolia, E. pallida, E. purpuyrea* or Interferon Alpha Summary This example hypothetically illustrates that extracts of different parts of *Echinacea angustifolia, E. pallida, E. purpuyrea* plants can may have different effects upon phosphotyrosylprotein complex expression in human T cells. According to the present invention, potent extracts of these plants can be identified by examining the expression of phosphotyrosyl protein complexes in cells treated with extracts and comparing such expression to that observed for a known stimulator of human T cells, interferon-alpha (α-INF). Thus, an extract may have clinical benefits when the pattern of phosphoprotein complexes expressed in cells treated with an Echinacea extracts are similar to pattern induced by α-INF. As hypothetically illustrated by the present example, a leaf extract of *E. angustifolia* did not produce a pattern of human T cell phosphotyrosyl protein complex expression like that induced by α-INF. Hence, the *E. angustifolia* leaf extract may be a clinically unimportant portion of the herb. However, the combination of *E. angustifolia* root extract and *E. purpurea* leaf extract induced expression of several of the same phosphotyrosylprotein complexes as are observed in cells treated with α-INF, suggesting that these extracts possess immunostimulatory activity like that of α-INF. However, the expression of phosphotyrosylproteins observed for leaf extracts of *E. angustifolia* and *E. pallida* were dissimilar to that provided by α-INF, indicating that these leaf extracts may not stimulate T cells. Thus, the biological potency of a complex mixture may be determined without the need to separate the components of the mixture and without knowledge of the mechanism(s) of action of those components.

Methods

Chemicals: Anti-phosphotyrosine antibodies may be purchased from Upstate Biotechnology (Lake Placid, N.Y.). Alcohol extracts of the root of *Echinacea angustifolia* and *E. pallida* and alcohol extracts of the dried top portions of *E. angustifolia* and *E. purpurea* may be obtained from Botanical and Nutritional International, Inc. (Paterson, N.J.). Interferon alpha (α-INF) and all other chemicals are purchased from Sigma (St. Louis, Mo.) and are the highest purity commercially available.

Human T cell lines: The HL-60 cell line (CCL-240) is useful as a model for human T cells and may be obtained from the American Type Culture Collection (Bethesda, Md.). HL-60 cells are leukemia cells originally isolated from a 36-year old Caucasian female.

Cell Plating: HL-60 cells are propagated according to the instructions of the supplier in suspension. For experiments, cells are seeded from a log-phase culture at a density of $1\times10^5$ cells per mL in 100 mm plates, 20 mL per plate, 3 plates per treatment. Serum concentration in the test medium is maintained at 0.5%. After 24 hours, the Echinacea extracts are added in 10 µL dimethylsulfoxide (DMSO) to achieve a final concentrations of each extract of 100 µg/mL. Interferon-alpha (α-INF) is added to the incubation plates in 10 µL phosphate-buffered saline, pH 7.4 (PBS) to produce an effective concentration of 500 IU/mL. Controls are treated with 10 µL DMSO only.

On day two, 24 hours after the Echinacea extracts and α-INF are added, the HL-60 cells are collected by centrifugation at 4° C. The cell pellet is placed on wet ice and lysed for 20 minutes using 20 mM Tris buffer (pH 8.0) with 137 mM NaCl, 10% glycerol, 1% Nonidet P-40, 1 mM phenylmethyl-sulfonyl fluoride, 0.15 units/mL aprotinin, and 1 mM sodium orthovanadate. Cell lysates are collected after centrifugation at 30,000 rpm at 4° C. for 10 minutes to separate cellular debris from lysates.

Gel Electrophoresis and Immunoblotting: Techniques used are as described in Example 1, with the single modification that the SDS is eliminated. This modification allows the protein-protein complexes to remain intact.

Protein Determination: Spectrophotometric determination of protein concentration is described in Example 1.

Results

Figure 11:
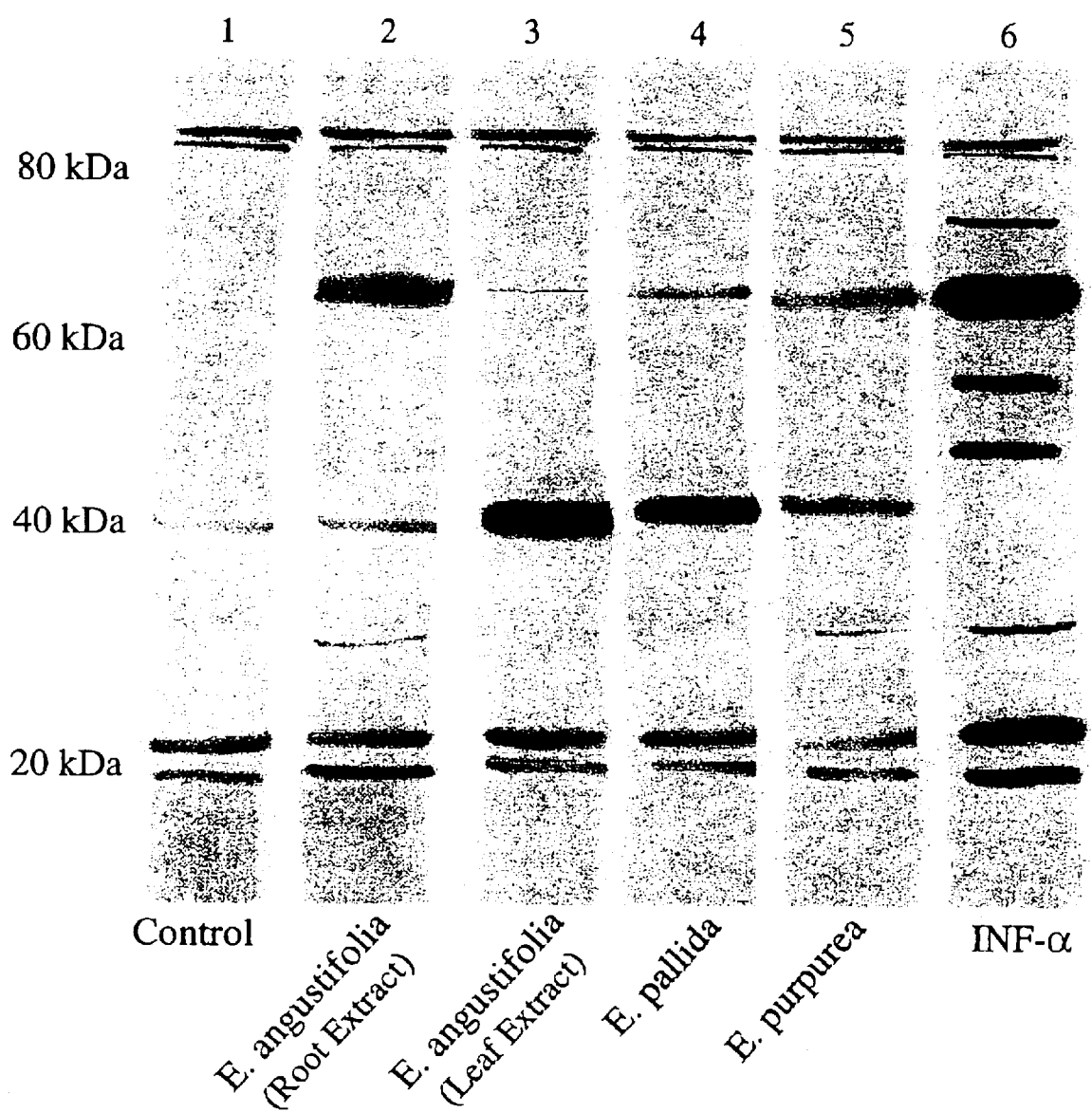
FIG. 11 provides a hypothetical protein blot to illustrate the type of phosphoprotein complexes that may be observed in quiescent HL60 cells treated with three different species of Echinacea or with interferon-alpha. Such protein complexes may be observed when nondenaturing conditions are used, for example, when SDS is not included during electrophoretic separation. Lanes 1 illustrates that five lightly-staining phosphoprotein complexes may hypothetically be observed in the molecular weight range of 15 to 90 kDa in quiescent HL-60 control cells. The molecular weights of these complexes are 19, 21, 40, 84 and 86 kDa. Incubation of HL-60 cells with 500 IU INFα/ml may give rise to expression of a number of phosphoprotein complexes, for example, the nine, darkly-staining bands depicted in lane 6. Several of these bands may represent new phosphoprotein complexes that are not seen in control cells but which may be induced by INFα treatment, for example, the four, dark bands at 30, 45, 50 and 68 kDa shown in lane 6. One or more bands may be eliminated after INFα treatment, for example, the lightly-staining band at 40 kDa (compare lanes 1 and 6). Other bands may increase in staining intensity after INFα treatment, for example, the four bands at 19, 21, 84 and 86 kDa (lane 6), indicating enhanced expression of these phosphotyrosylprotein complexes. Treatment with an herbal extract may result in enhanced expression of some of the phosphotyrosylprotein complexes induced by INFα treatment, for example, the bands at 30 and 68 kDa which are hypothetically induced by treatment with *E. angustifolia* root extract (lane 2) and *E. purpurea* leaf extract (lane 5). However, extracts from other sources, even different parts of the same plant may have a different effect, for example, leaf extracts of *E. angustifolia* (lane 3) and *E. pallida* (lane 4) hypothetically induce greater expression of the 40 kDa band and less expression of the 30 and 68 kDa bands.

Control HL-60 cells constitutively express five protein complexes which have phosphotyrosine residues and which are detected as five lightly-staining bands (FIG. 11, lane 1). The molecular weights of these complexes are 19, 21, 40, 84 and 86 kDa. Incubation of HL-60 cells with 500 IU α-INF/mL hypothetically induces the expression of nine, darkly-staining bands (FIG. 11, lane 6). As depicted in FIG. 11, the lightly-staining band at 40 kDa is hypothetically no longer visible, but the four constitutive bands at 19, 21, 84 and 86 kDa increase in staining intensity, indicating enhanced expression of these phosphotyrosylprotein complexes. Additional phosphoprotein complexes may be expressed in α-INF-treated cells, for example, the four, dark bands migrating at 30, 45, 50 and 68 kDa.

Incubation of HL-60 cells with the *E. angustifolia* root extract (FIG. 11 lane 2) is depicted as resulting in the expression of seven phosphotyrosylprotein complexes. Control HL-60 may express some or all of the same proteins. In this example, all five of the constitutive phosphotyrosine containing protein complexes that appear in control HL-60 cells are shown to appear in *E. angustifolia* root-treated HL-60 cells. Moreover, the staining intensity of these constitutive protein bands in root extract-treated cells is depicted as being similar to the staining intensity observed for control HL-60 cells. Some phosphotyrosylprotein complexes may be expressed in the *E. angustifolia* root-treated HL-60 cells that do not appear in untreated controls, for example, the phosphotyrosylprotein complexes migrating at 30 and 68 kDa. As depicted in FIG. 11, the 30 kDa complex stains as a single, thin, light band, while the 68 kDa complex is a wide, darker staining band. As also depicted in FIG. 11, these two protein complexes appear in the α-INF-treated HL-60 cells, which would indicate that such expression is correlated to T cell stimulation.

An extract from another part of the same plant may have a different effect upon the expression of phosphotyrosylprotein complexes. For example, six bands representing phosphotyrosylprotein complexes are depicted in FIG. 11 in HL-60 cells incubated with the leaf extract of *E. angustifolia* at 100 µg/mL (FIG. 11, lane 3). These protein complexes are depicted as migrating at 19, 21, 40, 68, 84 and 86 kDa. As illustrated by this example, the *E. angustifolia* root extract and leaf extract may induce the expression of different phosphotyrosylprotein complexes, for example, those at 30, 40, and 68 kDa. The leaf extract is depicted as having only the limited ability to induce expression of the 68 kDa phosphotyrosylprotein and no ability to induce expression of the 30 kDa phosphotyrosylprotein. Similarly, the leaf extract is depicted as inducing more expression of the 40 kDa phosphotyrosylprotein complex than the root extract.

Such differences would indicate that the pattern of phosphotyrosylprotein complex expression in HL-60 cells treated with the root extract of *E. angustifolia* is more similar to α-INF treatment than that of the leaf extract. Given these data, *E. angustifolia* leaf extract would be expected to have little immunostimulating activity because it does not induce expression of the same phosphotyrosylproteins as are induced by α-INF.

*E. pallida* leaf extract is depicted as inducing the expression of two phosphotyrosylprotein complexes in resting HL-60 cells (FIG. 11, lane 4). This response would be qualitatively similar to that of the leaf extract of *E. angustifolia*. However, the *E. pallida* leaf extract is depicted as inducing slightly less expression of the 40 kDa phosphotyrosylprotein complex and somewhat greater expression of the thin phosphotyrosylprotein complex at 68 kDa. The strong similarity in phosphotyrosylprotein complex expression between the leaf extract of *E. pallida* and *E. angustifolia* and their differences from α-INF would indicate that both leaf extracts have little immunostimulating activity.

However, the leaf extract of *E. purpurea* is depicted as inducing the expression of three phosphotyrosylprotein complexes: a slight band at 30 kDa, a wide band at 40 kDa, and a thick band at 68 kDa (FIG. 11, lane 5). Thus, *E. purpurea* may induce expression of some of the same phosphotyrosylprotein complexes as α-INF, for example, those at 30 kDa and 68 kDa. Such results would indicate that the *E. angustifolia* root extract and the *E. purpurea* leaf extract may stimulate T cells and thereby enhance the immune response against infection.

Interpretation

The Immune System: One way to combat colds and flu infections is to stimulate the body's own immune system to resist the unwanted microorganisms. The main effector cells of the immune system are: (i) macrophages that engulf microorganisms directly, (ii) T lymphocytes (T cells) that protect against intracellular diseases and cellular neoplasms, and (iii) B lymphocytes that develop into plasma cells that secrete antibodies or immunoglobulins in response to certain antigens. Biological response modifiers (BRMs) or immunostimulants may affect either the cellular or humoral immune system or both. They are nonspecific in character, producing general stimulation of the entire system. Because the response capacity of the immune system is limited, BRMs are more effective when used in conjunction with other chemotherapeutic agents or when the disease entity is quantitatively small.

Echinacea: Of all of the nonspecific immunostimulants of plant origin, the most comprehensively studied is echinacea. This name originally referred to the dried rhizome and roots of *E. angustifolia* DC., the narrow-leaved purple coneflower, but it was often confused with *E. pallida*, the pale purple coneflower, and with *E. purpurea*, the purple coneflower.

Echinacea has no direct bactericidal or bacteriostatic properties. Its beneficial effects in the treatment of bacterial and viral infections are thought to be brought about by its ability to act as an immunostimulant. It appears to increase phagocytosis and promote the activity of the lymphocytes, resulting in the increased release of tumor necrosis factor. Hyaluronidase activity is inhibited, and the activity of the adrenal cortex is stimulated. There are also indications that it induces the production of interferon. All of these actions tend to increase the body's resistance to bacterial and viral infections.

To date, more than three hundred chemical, pharmacological and clinical studies have been conducted on Echinacea, mostly by European research groups. Rather than relying on a single chemical component, research suggests that the synergistic action of several chemical groups from the herb and the root of *E. angustifolia* and *E. purpurea* contribute to the mechanism of immunomodulation by this plant. Thus, the usual pharmacological separation techniques do not adequately quantify the potency of these therapeutic botanical extracts.

This example illustrates the types of tyrosylphosphorylated protein complexes which may be expressed in resting immune cells when those cells are stimulated with a complex botanical mixture. Such expression patterns may be compared with the expression patterns induced by natural cytokines such as α-INF. According to the present invention, when similar patterns of tyrosylphosphorylated protein expression are observed for a new plant extract and a known cytokine, the plant extract will have physiological activities similar to the known cytokine.

What is claimed is:

1. A method for determining whether a plant extract has bioloaical activity, which method comprises incubating the plant extract with cultured mammalian cells to produce tested mammalian cells, lysing said tested mammalian cells to produce a mixture of cellular proteins, electrophoretically-separating said mixture of cellular proteins, reacting said mixture of cellular proteins with a labeled monoclonal or polyclonal antibody directed against phosphorylated amino acids and comparing the pattern of phosphorylation produced by five or more cellular proteins of said mixture of cellular proteins in said tested mammalian cells to the pattern of phosphorylation produced by five or more cellular proteins of a mixture of cellular proteins in control cells; wherein said control cells are said cultured mammalian cells which have not been exposed to said plant extract, and wherein differences in said pattern of phosphorylation produced in said tested mammalian cells as compared to said pattern of phosphorylation produced in said control cells indicates biological activity of said plant extract.

2. The method of claim 1 wherein said plant extract is an extract of saw palmetto.

3. The method of claim 1 wherein said plant extract is an extract of saw palmetto combined with any one of lycopene, methylcobalamine and ursolic acid.

4. The method of claim 1 wherein said plant extract is a root extract of *Echinacea augustifolia*.

5. The method of claim 1 wherein said plant extract is a root extract of *Echinacea purpurea*.

6. The method of claim 1 wherein said control cells are quiescent.

7. The method of claim 1 which further comprises comparing the pattern of phosphorylation produced by five or more cellular porteins of said mixture of cellular proteins in said tested mammalian cells to the pattern of phosphorylation produced by five or more cellular proteins of a mixture of cellular proteins in positive control cells.

8. The method of claim 7 wherein said positive control cells are said cultured mammalian cells which have been exposed to a beneficial and non-toxic compound.

9. The method of claim 8 wherein said beneficial and non-toxic compound is a Food and Drug Administration approved drug.

10. The method of claim 8 wherein said beneficial and non-toxic compound is a beneficial plant or herbal extract of proven efficacy.

11. The method of claim 7 wherein said phosphorylated amino acid is a phosphorylated serine, phosphorylated threonine or phosphorylated tyrosine.

12. The method of claim 7 wherein said pattern of phosphorylation produced by five or more cellular proteins of a mixture of cellular proteins in control cells is visualized using monoclonal or polyclonal antibodies directed against phosphorylated serine, phosphorylated threonine or phosphorylated tyrosine.

13. The method of claim 1 wherein said monoclonal antibodies are conjugated to a reporter molecule.

\* \* \* \* \*